(12) United States Patent
Fan et al.

(10) Patent No.: US 11,938,154 B2
(45) Date of Patent: Mar. 26, 2024

(54) COMPOSITIONS AND METHODS FOR TREATING AND/OR PREVENTING SEPSIS AND/OR INFLAMMATORY CONDITIONS

(71) Applicant: MUSC Foundation for Research Development, Charleston, SC (US)

(72) Inventors: Hongkuan Fan, Charleston, SC (US); Andrew Goodwin, Mount Pleasant, SC (US); Perry V. Halushka, Charleston, SC (US); James A Cook, Mount Pleasant, SC (US); Yue Zhou, San Francisco, CA (US)

(73) Assignee: MUSC Foundation for Research Development, Charleston, SC (US)

( * ) Notice: Subject to any disclaimer, the term of this patent is extended or adjusted under 35 U.S.C. 154(b) by 132 days.

(21) Appl. No.: 16/959,030

(22) PCT Filed: Feb. 27, 2019

(86) PCT No.: PCT/US2019/019822
§ 371 (c)(1),
(2) Date: Jun. 29, 2020

(87) PCT Pub. No.: WO2019/168977
PCT Pub. Date: Sep. 6, 2019

(65) Prior Publication Data
US 2020/0390822 A1 Dec. 17, 2020

Related U.S. Application Data

(60) Provisional application No. 62/635,913, filed on Feb. 27, 2018.

(51) Int. Cl.
| | | |
|---|---|---|
| *A61K 35/44* | (2015.01) | |
| *A61K 38/19* | (2006.01) | |
| *A61P 11/00* | (2006.01) | |
| *A61P 31/04* | (2006.01) | |

(52) U.S. Cl.
CPC ............ *A61K 35/44* (2013.01); *A61K 38/195* (2013.01); *A61P 11/00* (2018.01); *A61P 31/04* (2018.01)

(58) Field of Classification Search
CPC ............................................. C12N 15/11–117
See application file for complete search history.

(56) References Cited

U.S. PATENT DOCUMENTS

| | | | |
|---|---|---|---|
| 2011/0160086 A1 | 6/2011 | Rosenfeld | |
| 2011/0165128 A1 | 7/2011 | Doronin | |
| 2016/0082049 A1* | 3/2016 | Chen ................... | A61K 35/51 536/24.5 |
| 2016/0108368 A1* | 4/2016 | Larocca ............... | C12N 5/0692 435/317.1 |
| 2017/0258840 A1 | 9/2017 | Mitsialis | |

FOREIGN PATENT DOCUMENTS

EP 2446929 A1 * 5/2012 .......... A61K 9/5176

OTHER PUBLICATIONS

Ma et al. "Moderate Exercise Enhances Endothelial Progenitor Cell Exosomes Release and Function" . Med. Sci. Sports Exerc., vol. 50, No. 10, pp. 2024-2032, 2018 (Year: 2018).*
International Search Report and Written Opinion of the International Searching Authority Corresponding to International application No. PCT/US2019/19822 dated Jun. 18, 2019.
Fan et al., "Endothelial Progenitor Cells and a Stromal Cell-derived Factor-1a Analogue Synergistically Improve Survival in Sepsis", American Journal of Respiratory And Critical Care Medicine, vol. 189, No. 12, pp. 1509-1519 (2014).
Cantaluppi V, et al., (2012) "Microvesicles derived from endothelial progenitor cells protect the kidney from ischemia-reperfusion injury by microRNA-dependent reprogramming of resident renal cells," Kidney Int; 82: pp. 412-427.
Cerutti C, et al., (2017) "MiR-126 and miR-126* regulate shear-resistant firm leukocyte adhesion to human brain endothelium," Sci Rep; 7: 45284, pp. 1-14.
Chen DC.(2017) "Sepsis and Intestinal Microvascular Endothelial Dysfunction,". Chin Med J (Engl); 130: pp. 1137-1138.
Coletta C, et al., (2014) "Endothelial dysfunction is a potential contributor to multiple organ failure and mortality in aged mice subjected to septic shock: preclinical studies in a murine model of cecal ligation and puncture," Crit Care; 18: 511. 15 Pages.
Fan H, et al., (2014) "Endothelial progenitor cells and a stromal cell-derived factor-1alpha analogue synergistically improve survival in sepsis," Am J Respir Crit Care Med; 189: pp. 1509-1519.
Fish JE, et al., (2008) "miR-126 regulates angiogenic signaling and vascular integrity," Dev Cell ; 15: pp. 272-284.
Guldner A, et al., (2015) "Expanded endothelial progenitor cells mitigate lung injury in septic mice," Stem Cell Res Ther; 6:pp. 230.
Harris TA, et al., (2008). "MicroRNA-126 regulates endothelial expression of vascular cell adhesion molecule 1.," Proc Natl Acad Sci U S A; 105: pp. 1516-1521.
International Preliminary Report on Patentability and Written Opinion of International Searching Authority corresponding to U.S Application PCT/US 2019/019822 dated Jun. 18, 2019.

(Continued)

*Primary Examiner* — Thane Underdahl
(74) *Attorney, Agent, or Firm* — Jenkins, Taylor & Hunt, P.A.

(57) ABSTRACT

The presently disclosed subject matter relates to isolated compositions and methods for treating and/or preventing sepsis and inflammatory conditions, such as Acute Respiratory Distress Syndrome (ARDS). In some embodiments, the presently disclosed subject matter relates to endothelial progenitor cell-derived exosomes to treat and/or prevent sepsis and inflammatory conditions, such as Acute Respiratory Distress Syndrome (ARDS). The endothelial progenitor cell-derived exosomes can be modified to overexpress one or more miRNAs.

19 Claims, 13 Drawing Sheets
Specification includes a Sequence Listing.

(56) References Cited

OTHER PUBLICATIONS

Li X, et al., (2016) "Exosomes derived from endothelial progenitor cells attenuate vascular repair and accelerate reendothelialization by enhancing endothelial function," Cytotherapy; 18: pp. 253-262.

Wang S, et al., (2008) "The endothelial-specific microRNA miR-126 governs vascular integrity and angiogenesis," Dev Cell; 15:pp. 261-271.

Xu X, et al., (2015) "Role of Endothelial Progenitor Cell Transplantation in Rats With Sepsis," Transplant Proc; 47: pp. 2991-3001.

Yang H, et al., (2004). "Reversing established sepsis with antagonists of endogenous high-mobility group box 1," Proc Natl Acad Sci U S A; 101: pp. 296-301.

Zernecke A, et al., (2009). "Delivery of microRNA-126 by apoptotic bodies induces CXCL12-dependent vascular protection," Sci Signal; 2: ra81.

Zhang J, et al., (2016) "Exosomes Derived from Human Endothelial Progenitor Cells Accelerate Cutaneous Wound Healing by Promoting Angiogenesis Through Erk1/2 Signaling," Int J Biol Sci; 12: pp. 1472-1487.

Zhou Y, et al.,(2018) "Exosomes from Endothelial Progenitor Cells Improve the Outcome of a Murine Model of Sepsis." Mol Ther: 26: pp. 1375-1384.

\* cited by examiner

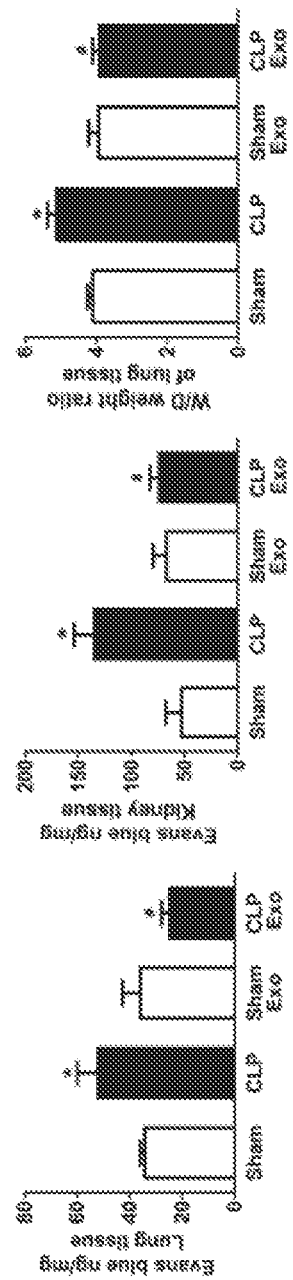

COMPOSITIONS AND METHODS FOR TREATING AND/OR PREVENTING SEPSIS AND/OR INFLAMMATORY CONDITIONS

RELATED APPLICATIONS

This application is a national stage filing of PCT International Application No. PCT/US2019/019822, filed Feb. 27, 2019, incorporated herein by reference in its entirety, which claims priority to and the benefit of U.S. Provisional Application Ser. No. 62/635,913, filed Feb. 27, 2018, the disclosure of which is incorporated herein by reference in its entirety.

GRANT STATEMENT

This invention was made with government support under Grant Nos. 1R01GM113995, 1K23HL135263-01A1, and UL1TR001450 awarded by the National Institutes of Health. The government has certain rights in the invention.

TECHNICAL FIELD

The presently disclosed subject matter relates to isolated compositions and methods for treating and/or preventing sepsis and inflammatory conditions, such as Acute Respiratory Distress Syndrome (ARDS). In some embodiments, the presently disclosed subject matter relates to endothelial progenitor cell-derived exosomes to treat and/or prevent sepsis and/or inflammatory conditions, such as Acute Respiratory Distress Syndrome (ARDS). In some embodiments, the endothelial progenitor cell-derived exosomes have been modified to overexpress one or more miRNAs

BACKGROUND

Sepsis is defined as life-threatening organ dysfunction caused by a dysregulated host response to infection[1-3]. Previous studies have shown that microvascular damage occurs early in sepsis and can result in multi-organ dysfunction and ultimately death[4,5]. The endothelium plays a pivotal role in governing microvascular permeability and, thus, regulates organ perfusion and homeostasis. Microvascular injury disrupts endothelial cell tight junctions leading to impaired barrier integrity and activates endothelial cells leading to inflammatory cytokine release and expression of cell adhesion markers[6,7]. These derangements lead to organ edema, local perpetuation of inflammation, and leukocyte trafficking and play a pivotal role in the development of sepsis-related organ failure[8-11]. Despite this, there are no available pharmacological agents to ameliorate the endothelial dysfunction in sepsis.

The acute respiratory distress syndrome (ARDS) is a complex and deadly disease characterized by inflammation and lung permeability leading to alveolar edema, hypoxemia and organ failure (Thompson B T, et al., *N Engl J Med* 2017; 377: 562-572; Rawal G, et al., *J Transl Int Med* 2018; 6: 74-77). ARDS occurs in up to 10% of patients admitted to an intensive care unit with mortality rates ranging from 35% to 46% (Pais F M, et al., *Respir Care* 2018; 63: 1060-1069; Bellani G, et al. *JAMA* 2016; 315: 788-800). To date, there are no approved pharmacological treatments for this syndrome. The acute lung injury (ALI) associated with ARDS is characterized by damage and disruption of the epithelial and endothelial layers at the alveolar-capillary barrier and recruitment of inflammatory cells into the alveolar space. However, a complete understanding of the mechanisms of action in ALI remains in knowledge in the art.

Endothelial progenitor cells (EPCs) play a crucial role in maintaining vascular homeostasis and facilitating vascular repair[12]. Previous studies have demonstrated that administration of EPCs have beneficial effects on vascular injury, organ dysfunction, and mortality in a preclinical model of sepsis[13-15]. In addition to repopulating injured endothelium, emerging data suggest that EPCs could also modulate endothelial health through the release of paracrine mediators such as exosomes[16-18]. Exosomes are membranous nanovesicles, 30-120 nanometers in size, secreted from the endosomal compartment of cells. They mediate intercellular communication via transferring bioactive molecules, including microRNAs (miRNAs). MicroRNAs are non-coding RNAs that bind to messenger RNAs and inhibit gene expression at the post-transcriptional level. Several studies have suggested that exosomal miRNAs can be taken up by recipient cells with resultant modulation of cellular gene expression and function[19]. Further, recent investigations suggest that miRNAs play a major role in mediating the impact of exosomes on recipient cells[20,21] and have therapeutic potential in endothelial cell dysfunction[22,23]. MiR-126, in particular, serves as a crucial regulator of several endothelial cell functions including angiogenesis, vascular repair, inflammatory activation and apoptosis[24]. Both miR-126-3p and 5p target genes relevant to endothelial activation and inflammation including vascular cell adhesion molecule 1 (VCAM1) and high mobility group box 1 (HMGB1), respectively (25-27). However, the role of exosomes and exosomal miR-126-3p and 5p in the microvascular dysfunction of sepsis remains unknown.

Thus, there is therefore a need for new compositions and methods for treating and/or preventing sepsis and/or inflammatory conditions.

SUMMARY

In accordance with the presently disclosed subject matter, provided in some embodiments is a method for treating and/or preventing sepsis in a subject. In some embodiments, the method comprising administering to a subject a composition comprising, consisting essentially of, or consisting of a therapeutically effective amount of endothelial progenitor cell-derived exosomes.

In accordance with the presently disclosed subject matter, provided in some embodiments is a method for treating and/or preventing an inflammatory condition in a subject. In some embodiments, the method comprises administering to a subject a composition comprising, consisting essentially of, or consisting of a therapeutically effective amount of endothelial progenitor cell-derived exosomes. In some embodiments, the inflammatory condition is selected from the group consisting of respiratory distress syndrome (ARDS), acute lung injury (ALI), acute kidney injury (AKI), acute liver injury (ALI), delirium, shock, capillary leak syndrome, and combinations thereof.

In accordance with the presently disclosed subject matter, provided in some embodiments is the use of a pharmaceutical composition comprising, consisting essentially of, or consisting of a therapeutically effective amount of endothelial progenitor cell-derived exosomes to treat and/or prevent sepsis in a subject.

In accordance with the presently disclosed subject matter, provided in some embodiments is the use of a therapeutically effective amount of endothelial progenitor cell-derived exosomes for the preparation of a medicament to treat and/or prevent sepsis in a subject.

In accordance with the presently disclosed subject matter, provided in some embodiments is provided is a pharmaceutical composition comprising, consisting essentially of, or consisting of a therapeutically effective amount of endothelial progenitor cell-derived exosomes for treating and/or preventing sepsis in a subject.

In accordance with the presently disclosed subject matter, provided in some embodiments is the use of a pharmaceutical composition comprising, consisting essentially of, or consisting of a therapeutically effective amount of endothelial progenitor cell-derived exosomes to treat and/or prevent an inflammatory condition in a subject.

In accordance with the presently disclosed subject matter, provided in some embodiments is the use of a therapeutically effective amount of endothelial progenitor cell-derived exosomes for the preparation of a medicament to treat and/or prevent an inflammatory condition in a subject.

In accordance with the presently disclosed subject matter, provided in some embodiments is a pharmaceutical composition comprising, consisting essentially of, or consisting of a therapeutically effective amount of endothelial progenitor cell-derived exosomes for treating and/or preventing an inflammatory condition in a subject.

In some embodiments of the presently disclosed methods, use, and/or compositions, the inflammatory condition is selected from the group consisting of respiratory distress syndrome (ARDS), acute lung injury (ALI), acute kidney injury (AKI), acute liver injury (ALI), delirium, shock, capillary leak syndrome, and combinations thereof.

In some embodiments of the presently disclosed methods, use, and/or compositions, the endothelial progenitor cell-derived exosomes have been modified to enhance expression of an miR-126 microRNA. In some embodiments of the presently disclosed methods, use, and/or compositions, the at least one modification that results in enhancement of expression of an mir-126 microRNA in the endothelial progenitor cell-derived exosomes comprises a modification selected from the group consisting of transfection of the endothelial progenitor cell-derived exosomes with a nucleic acid molecule that encodes the miR-126 microRNA or a precursor thereof, transfection of an endothelial progenitor cell with a nucleic acid molecule that encodes the miR-126 microRNA or a precursor thereof, introduction into the endothelial progenitor cell-derived exosomes of an expression construct that expresses the miR-126 microRNA or a precursor thereof in the endothelial progenitor cell-derived exosomes, introduction into an endothelial progenitor cell of an expression construct that expresses the miR-126 microRNA or a precursor thereof in the endothelial progenitor cell, treatment of the endothelial progenitor cell-derived exosomes with an SDF-1α polypeptide or an agonist or mimetic thereof, and/or treatment of an endothelial progenitor cell with an SDF-1α polypeptide or an agonist or mimetic thereof.

In accordance with the presently disclosed subject matter, provided in some embodiments is an endothelial progenitor cell-derived exosome, wherein the endothelial progenitor cell-derived exosome comprises one or more modifications that enhance expression of an miR-126 microRNA in the endothelial progenitor cell-derived exosome.

In some embodiments, the least one of the one or more modifications comprises a heterologous nucleotide sequence that comprises, consists essentially of, or consists of one or more of SEQ ID NOs: 1-3. In some embodiments, the heterologous nucleotide sequence is operatively linked to one or more transcriptional regulatory sequences. In some embodiments, the endothelial progenitor cell-derived exosome comprises a stromal cell-derived factor 1 (SDF1)/C—X—C motif chemokine 12 (CXCL12) gene product and/or a mimetic thereof. In some embodiments, the mimetic thereof is CTCE-0214 (CTCE).

In accordance with the presently disclosed subject matter, provided in some embodiments is a pharmaceutical composition comprising the endothelial progenitor cell-derived exosome in accordance with the presently disclosed subject matter and a pharmaceutically acceptable carrier, optionally a pharmaceutically acceptable carrier that is pharmaceutically acceptable for use in a human. In some embodiments, the endothelial progenitor cell-derived exosome comprises a stromal cell-derived factor 1 (SDF1)/C—X—C motif chemokine 12 (CXCL12) gene product and/or a mimetic thereof. In some embodiments, the mimetic thereof is CTCE-0214 (CTCE).

In accordance with the presently disclosed subject matter, provided in some embodiments is a pharmaceutical composition to treat and/or prevent sepsis and/or an inflammatory condition in a subject.

It is an object of the presently disclosed subject matter to provide compositions and methods for treating and/or preventing sepsis and/or inflammatory conditions.

An object of the presently disclosed subject matter having been stated hereinabove, and which is achieved in whole or in part by the compositions and methods disclosed herein, other objects will become evident as the description proceeds when taken in connection with the accompanying Figures as best described herein below.

BRIEF DESCRIPTION OF THE DRAWINGS

FIGS. 3A-3H are a series of graphs showing the effect of EPC-exosomes on organ dysfunction, vascular leakage, and lung edema in CLP-induced sepsis. Plasma levels of AST (FIG. 3A), ALT (FIG. 3B), and BUN (FIG. 3C) were measured at 24 h post CLP. *$p<0.05$ compared with sham group, #$p<0.05$ compared with CLP group. N=3-6 mice per group. Lung (FIG. 3D) and renal (FIG. 3E) injury scores were assessed. *$p<0.05$ compared to sham group, #$p<0.05$ compared to CLP group. N=3-4 mice per group. Vascular leakage in lung (FIG. 3F) and kidney (FIG. 3G) were measured via injecting Evans' blue dye at 24 h post CLP. Lung water content was determined by wet (W)/dry (D) lung tissue weight ratio (FIG. 3H). *$p<0.05$ compared with sham group, #$p<0.05$ compared with CLP group. N=3-6 mice per group.

(FIGS. 8A-8B): Bar graphs showing exosome size distribution and concentration, which were measured by nanoparticle tracking analysis (NTA) with ZetaView. (FIG. 8C) is a digital image of a bar graphs showing detection of exosome markers including CD9, CD63, CD81 in EPC-exosomes and NIH3T3-exosomes by western blot.

BRIEF DESCRIPTION OF THE SEQUENCE LISTING

Figure 1:
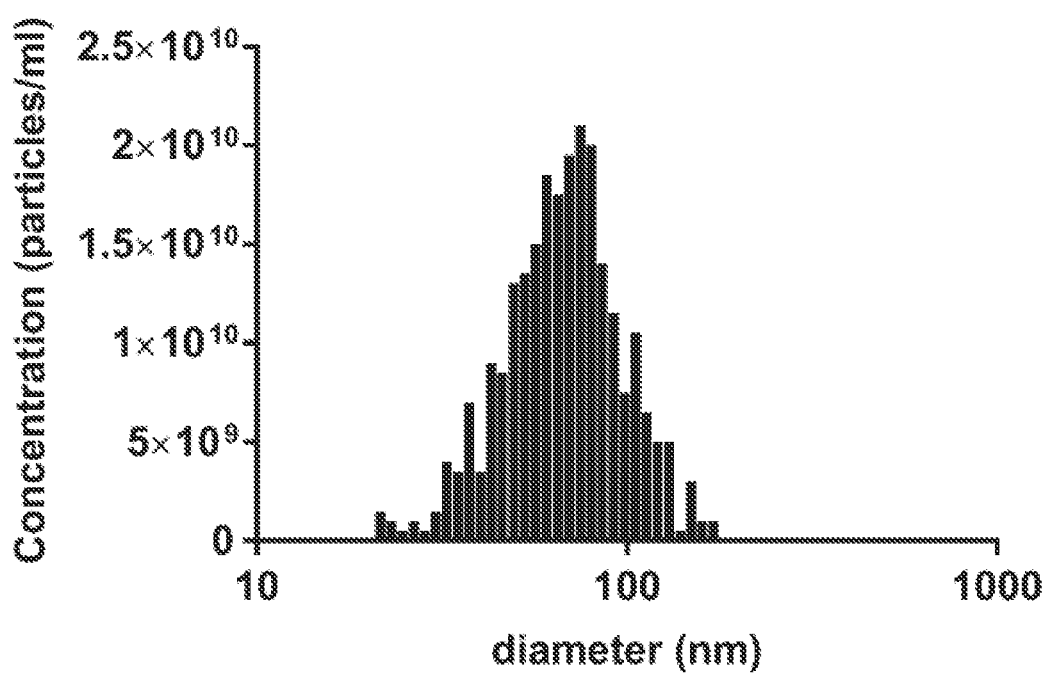
FIG. 1 is a bar graph of size distribution and total particle number of EPC-exosomes. The number of particles vs. particle size was generated by nanoparticle tracking analysis with Zetaview.

```
SEQ ID NO: 1: Homo sapiens microRNA 126 (MIR126);
GENBANK® biosequence database Accession
No. NR_029695.1
cgctggcgac gggacattat tacttttggt acgcgctgtg acacttcaaa
     10          20         30         40         50 ctcgtaccgt gagtaataat gcgccgtcca cggca
     60          70         80      85

SEQ ID NO: 2: Homo sapiens hsa-miR-126-3p; miRBase
Accession No. MIMAT0000445 (corresponds to
nucleotides 52-73 of SEQ ID NO: 1)
ucguaccgug aguaauaaug cg
     10          20

SEQ ID NO: 3: Homo sapiens hsa-miR-126-5p; miRBase
Accession No. MIMAT0000444 (corresponds to
nucleotides 15-35 of SEQ ID NO: 1)
cauuauuacu uuugguacgc g
     10          20
```

-continued

SEQ ID NOs: 4 & 5: CTCE-0214 (CTCE)
KPVSLSYRCPCRFF-Linker-LKWIQEYLEN-OH

SEQ ID NOs: 6 & 5: CTCE-0214 (CTCE)
KPVSLSYRAPFRFF-Linker-LOVIQEYLEKALN-OH

SEQ ID Nos: 7- 9:
Mouse miR-126 precursor:
GCACAUUAUUACUUUUGGUACGCGCUGUGACACUUCAAACUCGUACC

GUGAGUAAUAAUGCGC

Mouse miR-126-5p:
cauuauucuuuugguacgcg

Mouse miR-126-3p:
ucguaccgugaguaauaaugcg

DETAILED DESCRIPTION

The presently disclosed subject matter relates in some embodiments to the discovery that EPC-derived exosomes are beneficial in sepsis and can modulate endothelial cell function, in part, via the transfer of miR-126. More particularly, the impact of EPC-derived exosomes on survival, organ failure, and inflammation in the cecal ligation and puncture (CLP) model of sepsis was investigated, and the role of exosomal miR-126 in endothelial activation and sepsis survival was examined. The data disclosed herein confirmed a role for exosomal miR-126 in sepsis and suggest that it could present a therapeutic option for the treatment of sepsis induced endothelial cell dysfunction.

Additionally, experiments were performed in an ARDS model. It was found that EPC exosomes are beneficial for this as well. Thus, provided in accordance with some embodiments of the presently disclosed subject matter are methods and compositions for treating inflammatory conditions such as but not limited to acute respiratory distress syndrome (ARDS), acute lung injury (ALI), acute kidney injury (AKI), acute liver injury (ALI), delirium, shock, and capillary leak syndrome.

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

I. Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the presently disclosed subject matter and the claims.

Following long-standing patent law convention, the terms "a", "an", and "the" refer to "one or more" when used in this application, including the claims. For example, the phrase "an miRNA" refers to one or more miRNAs, including a plurality of the same miRNA. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods. Accordingly, unless indicated to the contrary, the numerical parameters set forth in this specification and attached claims are approximations that can vary depending upon the desired properties sought to be obtained by the presently disclosed subject matter.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. It is noted that, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter. For example, a pharmaceutical composition can "consist essentially of" a pharmaceutically active agent or a plurality of pharmaceutically active agents, which means that the recited pharmaceutically active agent(s) is/are the only pharmaceutically active agent(s) present in the pharmaceutical composition. It is noted, however, that carriers, excipients, and other inactive agents can and likely would be present in the pharmaceutical composition.

With respect to the terms "comprising", "consisting of", and "consisting essentially of", where one of these three terms is used herein, the presently disclosed and claimed subject matter can include the use of either of the other two terms. For example, in some embodiments, the presently disclosed subject matter relates to compositions comprising modified exosomes. It would be understood by one of ordinary skill in the art after review of the instant disclosure that the presently disclosed subject matter thus encompasses compositions that consist essentially of the modified exosomes of the presently disclosed subject matter, as well as compositions that consist of the modified exosomes of the presently disclosed subject matter.

As used herein m the term "CTCE-0214" (CTCE) refers to a stable peptide mimetic of SDF-1. In some embodiments, CTCE has the sequence KPVSLSYRCPCRFF-Linker-LKWIQEYLEKALN-OH (SEQ ID NOs: 4 and 5) or the sequence KPVSLSYRAPFRFF-Linker-LKWIQEY-LEKALN-OH (SEQ ID NOs: 6 and 5), and is available from British Canadian BioSciences, Vancouver, British Columbia, Canada.

As used herein, the term "miR-126" refers to a microRNA that is expressed in endothelial cells and corresponds to Accession No. NR_029695.1 of the GENBANK® biosequence database (SEQ ID NO: 1). The 85 nucleotide precursor miRNA is processed to at least two different forms, with the human form has-miR-126-5p corresponding to nucleotides 15-35 of NR_029695.1 (SEQ ID NO: 3) and the human form has-miR-126-3p corresponding to nucleotides 52-73 of NR_029695.1 (SEQ ID NO: 2). Given that the functions of microRNAs derive from sequence-specific interactions between themselves and their targets, miR-126-3p and miR-126-5p are known to target different gene products. For example, miR-126-3p is known to target vascular cell adhesion molecule 1 (VCAM1) and miR-126-5p is known to target high mobility group box 1 (HMGB1). Representative mouse sequences are also listed herein below.

The term "inflammatory condition" is meant to refer to a condition in a subject comprising an inflammation response. Such responses can occur in response to sepsis or alternative conditions and include but are not limited to: vascular leakage, immune system activation, immune cell migration/infiltration, tachycardia, hypotension, tachypnea, fever, leukocytosis, and organ injury and failure. Representative inflammatory conditions include but are not limited to acute respiratory distress syndrome (ARDS), acute lung injury (ALI), acute kidney injury (AKI), acute liver injury (ALI), delirium, shock, and capillary leak syndrome.

The term "subject" as used herein refers to a member of any invertebrate or vertebrate species. Accordingly, the term "subject" is intended to encompass any member of the Kingdom Animalia including, but not limited to the phylum Chordata (e.g., members of Classes Osteichythyes (bony fish), Amphibia (amphibians), Replia (reptiles), Aves (birds), and Mammalia (mammals)), and all Orders and Families encompassed therein.

The compositions and methods of the presently disclosed subject matter are particularly useful for warm-blooded vertebrates. Thus, the presently disclosed subject matter concerns mammals and birds. More particularly provided are compositions and methods derived from and/or for use in mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also provided is the use of the disclosed methods and compositions on livestock, including but not limited to domesticated swine (pigs and hogs), ruminants, horses, poultry, and the like.

"Exosomes" as used herein, means small membrane vesicles that are released into the extracellular environment following fusion of multivesicular bodies with the plasma membrane. Exosomes typically range in size from about 10 nm to about 120 nm in diameter, and are constitutively released from the cell in at least some form. Further, an exosome is an example of a vesicle, and in particular an example of an extracellular vesicle. Thus, the term "exosome" is also meant to include "extracellular vesicles". By "vesicle" is meant any spherical or semispherical molecule that comprises a lipid membrane, and is capable of fusing with other cells and other lipid membranes. The membrane may include proteins and cholesterols, which assist with cell fusion. The vesicle may contain substances such as nucleic acids, proteins, and chemicals. Thus, as used herein, the term "exosome" is also meant to include examples of vesicles, such as but not limited to exosomes (about 10 nm to about 100 nm in diameter), microvesicles (about 100 nm to about 300 nm in diameter), and apoptotic bodies (about 300 nm to about 500 nm in diameter). These small vesicles contain biologically active molecules, including miRNAs, nucleic acids, and protein, and have the ability to transfer these small molecules to another cell thereby influencing mRNA and protein expression.

As used herein a "formulation" means a formulation comprising an exosome or population of exosomes, in combination with a suitable agent. An "exosome formulation" also refers to a "compound" or "vesicle compound" present in, for example, PBS, normal saline, DMSO, and/or ethanol. An exosome formulation for intravenous delivery, for example by delivery from an IV bag comprises a vesicle or population of vesicles in combination with PBS and/or normal saline. A vesicle formulation for intravenous delivery, for example, by injection, comprises a vesicle or population of vesicles in combination with PBS and/or normal saline. A vesicle formulation for delivery via a medical device, for example a stent, valve, balloon or catheter comprises a vesicle or population of vesicles in combination with a formulated as a coating for a medical device as defined herein.

II. Modified Endothelial Progenitor Cell-Derived Exosomes and Methods of Producing the Same In some embodiments, the presently disclosed subject matter provides endothelial progenitor cell-derived exosomes, which in some embodiments have been modified to enhance expression of an miR-126 microRNA in the endothelial progenitor cell-derived exosome.

As used herein, the phrase "endothelial progenitor cell-derived exosomes" refers to exosomes that have been released from and/or produced by endothelial progenitor cells in vivo, ex vivo, and/or in vitro. Endothelial progenitor cell-derived exosomes can be isolated and/or prepared as described herein and then employed with or without additional modifications.

In some embodiments, the presently disclosed endothelial progenitor cell-derived exosomes have been manipulated to include at least one modification that increases the amount of an miR-126 nucleic acid(s) in the endothelial progenitor cell-derived exosomes per se and/or that delivers to a cell with which the endothelial progenitor cell-derived exosomes interact a nucleic acid that encodes an miR-126 nucleic acid. In some embodiments, the nucleic acid comprises a heterologous nucleotide sequence that comprises, consists essentially of, or consists of one or more of SEQ ID NOs: 1-3.

In those embodiments where the nucleic acid comprises a heterologous nucleotide sequence, in some embodiments the heterologous nucleotide sequence is operatively linked to one or more transcriptional regulatory sequences that permit expression of the heterologous nucleotide sequence in a target cell such as, but not limited to an endothelial cell that as a consequence of sepsis has reduced function.

The endothelial progenitor cell-derived exosomes of the presently disclosed subject matter can in some embodiments be provided in a composition that further comprises additional biologically active components. By way of example and not limitation, in some embodiments an endothelial progenitor cell-derived exosome as described herein further comprises a stromal cell-derived factor 1 (SDF1)/C—X—C motif chemokine 12 (CXCL12) gene product and/or an mimetic thereof, optionally in an amount sufficient to increase the amount of an miR-126 nucleic acid in the endothelial progenitor cell-derived exosomes per se and/or that delivers to a cell with which the endothelial progenitor cell-derived exosomes interact a nucleic acid that encodes an miR-126 nucleic acid. An exemplary mimetic is CTCE-0214 (CTCE), which is a peptide mimetic of SDF-1α that has the amino acid sequence set forth in SEQ ID NOs: 4-6.

In some embodiments, the presently disclosed subject matter provides a pharmaceutical composition comprising the endothelial progenitor cell-derived exosome as disclosed herein and a pharmaceutically acceptable carrier, optionally a pharmaceutically acceptable carrier that is pharmaceutically acceptable for use in a human. Pharmaceutical compositions of the presently disclosed subject matter can also further comprise a stromal cell-derived factor 1 (SDF1)/C—X—C motif chemokine 12 (CXCL12) gene product and/or a mimetic thereof such as, but not limited to CTCE.

Treatment or genetic modification to increase mir-126 can be done via the EPCs themselves, i.e. treating EPCs then obtaining the exosomes. One can modify an EPC in vitro and get exosomes from the in vitro modified EPCs. Treatment with CTCE can act in this manner. The EPCs are treated and then the exosomes are harvested. In some embodiments, the exosomes are generated in vitro, harvested, and administered intravenously. In some embodiments, the administration to a subject generates exosomes. In some embodiments, modifications of EPCs can be done genetically (introduce miR-126 coding sequence into an EPC under control of transcription regulatory elements that are active in EPCs), chemically (treat EPCs with SDF-1alpha or CTCE), or by transfecting miR-126 nucleic acids into the EPCs. Art recognized techniques can be employed as would be apparent to one of ordinary skill in the art upon a review of the instant disclosure. Representative, non-limiting techniques are described in U.S. Pat. Nos. 9,421,167 and 9,555,060, herein incorporated by reference.

III. Methods of Treating and/or Preventing Sepsis and/or Inflammatory Conditions The presently disclosed subject matter also provides methods for treating and/or preventing sepsis in subjects. In some embodiments, the presently disclosed methods comprise administering to a subject a composition comprising, consisting essentially of, or consisting of a therapeutically effective number of endothelial progenitor cell-derived exosomes as described herein.

The presently disclosed subject matter also provides methods for treating and/or preventing an inflammatory condition in a subject, the method comprising administering to a subject a composition comprising, consisting essentially of, or consisting of a therapeutically effective amount of endothelial progenitor cell-derived exosomes. In some embodiments the inflammatory condition is selected from the group consisting of respiratory distress syndrome (ARDS), acute lung injury (ALI), acute kidney injury (AKI), acute liver injury (ALI), delirium, shock, capillary leak syndrome, and combinations thereof.

The endothelial progenitor cell-derived exosomes employed in the presently disclosed methods can be freshly isolated and/or frozen endothelial progenitor cell-derived exosomes, either with or without post-isolation modifications designed to increase miR-126 levels in the endothelial progenitor cell-derived exosomes.

In some embodiments, the endothelial progenitor cell-derived exosomes are modified to enhance expression, e.g., to overexpress, an miR-126 microRNA relative to the level of expression of the miR-126 microRNA present in the endothelial progenitor cell-derived exosomes prior to the modification. Any method for increasing the expression of the miR-126 microRNA in the endothelial progenitor cell-derived exosomes can be employed in the presently disclosed methods. Exemplary modifications that can result in overexpression of an mir-126 microRNA in the endothelial progenitor cell-derived exosomes include transfection of the endothelial progenitor cell-derived exosomes with a nucleic acid molecule that encodes the miR-126 microRNA or a precursor thereof, introduction into the endothelial progenitor cell-derived exosomes of an expression construct that expresses the miR-126 microRNA or a precursor thereof in the endothelial progenitor cell-derived exosomes, and/or treatment of the endothelial progenitor cell-derived exosomes with an SDF-1α polypeptide or an agonist or mimetic thereof.

Endothelial progenitor cell-derived exosomes, modified and/or unmodified, can then be administered to subjects that either are experiencing sepsis or who are at risk for developing sepsis. In some embodiments, the endothelial progenitor cell-derived exosomes are administered to the subject in a therapeutically effective amount, which means that the number of endothelial progenitor cell-derived exosomes administered is sufficient to provide a protective or therapeutic benefit to the subject with respect to at least one symptom of sepsis.

Endothelial progenitor cell-derived exosomes, modified and/or unmodified, can then be administered to subjects that either are experiencing sepsis or who are at risk for developing an inflammatory condition as defined herein. In some embodiments, the endothelial progenitor cell-derived exosomes are administered to the subject in a therapeutically effective amount, which means that the number of endothelial progenitor cell-derived exosomes administered is sufficient to provide a protective or therapeutic benefit to the subject with respect to at least one symptom of an inflammatory condition as defined here. In some embodiments the inflammatory condition is selected from the group consisting of respiratory distress syndrome (ARDS), acute lung injury (ALI), acute kidney injury (AKI), acute liver injury (ALI), delirium, shock, capillary leak syndrome, and combinations thereof.

II.A. Formulations

An endothelial progenitor cell-derived exosome composition as described herein comprises in some embodiments a composition that includes a pharmaceutically acceptable carrier. Suitable formulations include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents.

The compositions used in the methods can take such forms as suspensions, solutions, or emulsions in oily or aqueous vehicles, and can contain formulatory agents such as suspending, stabilizing, and/or dispersing agents. The compositions used in the methods can take forms including, but not limited to peroral, intravenous, intraperitoneal, inhalation, intraprostatic, and intratumoral formulations. Alternatively or in addition, the active ingredient can be in powder form for constitution with a suitable vehicle (e.g., sterile pyrogen-free water) before use.

The formulations can be presented in unit-dose or multi-dose containers, for example sealed ampules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulfate). The tablets can be coated by methods known in the art. For example, a neuroactive steroid can be formulated in combination with hydrochlorothiazide, and as a pH stabilized core having an enteric or delayed-release coating which protects the neuroactive steroid until it reaches the colon.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring, and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt).

The compounds can also be formulated in rectal compositions (e.g., suppositories or retention enemas containing conventional suppository bases such as cocoa butter or other glycerides), creams or lotions, or transdermal patches.

In some embodiments, the presently disclosed subject matter employs an endothelial progenitor cell-derived exosome composition that is pharmaceutically acceptable for use in humans. One of ordinary skill in the art understands the nature of those components that can be present in an endothelial progenitor cell-derived exosome composition that is pharmaceutically acceptable for use in humans and also what components should be excluded from an endothelial progenitor cell-derived exosome composition that is pharmaceutically acceptable for use in humans.

III.B. Doses

As used herein, the phrases "treatment effective amount", "therapeutically effective amount", "treatment amount", and "effective amount" are used interchangeably and refer to an amount of a therapeutic composition sufficient to produce a measurable response (e.g., a biologically or clinically relevant response in a subject being treated). Actual dosage levels of active ingredients in the pharmaceutical compositions of the presently disclosed subject matter can be varied so as to administer an amount of the active compound(s) that is effective to achieve the desired therapeutic response for a particular subject. The selected dosage level can depend upon the activity of the therapeutic composition, the route of administration, combination with other drugs or treatments, the severity of the condition being treated, the condition and prior medical history of the subject being treated, etc. However, it is within the skill of the art to start doses of the compound at levels lower than required to achieve the desired therapeutic effect and to gradually increase the dosage until the desired effect is achieved.

The potency of a therapeutic composition can vary, and therefore a "therapeutically effective amount" can vary. However, one skilled in the art can readily assess the potency and efficacy of a candidate modulator of the presently disclosed subject matter and adjust the therapeutic regimen accordingly.

After review of the disclosure herein of the presently disclosed subject matter, one of ordinary skill in the art can tailor the dosages to an individual subject, taking into account the particular formulation, method of administration to be used with the composition, and other factors. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

Thus, in some embodiments the term "effective amount" is used herein to refer to an amount of an endothelial progenitor cell-derived exosome and/or a composition comprising the same sufficient to produce a measurable amelioration of a symptom associated with sepsis and/or to produce a measurable amelioration of an inflammatory condition or a symptom thereof. Actual dosage levels of active ingredients in an endothelial progenitor cell-derived exosome composition of the presently disclosed subject matter can be varied so as to administer an amount of endothelial progenitor cell-derived exosomes that is effective to achieve the desired response for a particular subject and/or application. The selected dosage level can depend upon a variety of factors including the activity of the endothelial progenitor cell-derived exosome composition, formulation, route of administration, combination with other drugs or treatments, severity of the condition being treated, and physical condition and prior medical history of the subject being treated. In some embodiments, a minimal dose is administered, and dose is escalated in the absence of dose-limiting toxicity to a minimally effective amount. Determination and adjustment of an effective dose, as well as evaluation of when and how to make such adjustments, are known to those of ordinary skill in the art.

For administration of an endothelial progenitor cell-derived exosome composition as disclosed herein, conventional methods of extrapolating human dosage based on doses administered to a murine animal model can be carried out using techniques known to one of ordinary skill in the art. For additional guidance regarding formulations and doses, see U.S. Pat. Nos. 5,326,902; 5,234,933; PCT International Publication No. WO 2013/048734; PCT International Publication No. WO 93/25521; Remington et al. (1975) *Remington's Pharmaceutical Sciences*, 15th ed., Mack Pub. Co., Easton, Pennsylvania; Goodman et al. (1996) *Goodman & Gilman's the Pharmacological Basis of Therapeutics*, 9th ed., McGraw-Hill Health Professions Division, New York; Berkow et al. (1997) *The Merck Manual of Medical Information, Home ed.*, Merck Research Laboratories, Whitehouse Station, New Jersey; Speight et al. (1997) *Avery's Drug Treatment: A Guide to the Properties, Choice, Therapeutic Use and Economic Value of Drugs in Disease Management*, 4th ed. Adis International, Auckland/Philadelphia.

III.C. Routes of Administration

The presently disclosed endothelial progenitor cell-derived exosome compositions can be administered to a subject in any form and/or by any route of administration. In some embodiments, the formulation is a sustained release formulation, a controlled release formulation, or a formulation designed for both sustained and controlled release. As used herein, the term "sustained release" refers to release of an active agent such that an approximately constant amount of an active agent becomes available to the subject over time. The phrase "controlled release" is broader, referring to release of an active agent over time that might or might not be at a constant level. Particularly, "controlled release" encompasses situations and formulations where the active ingredient is not necessarily released at a constant rate, but can include increasing release over time, decreasing release over time, and/or constant release with one or more periods of increased release, decreased release, or combinations thereof. Thus, while "sustained release" is a form of "controlled release", the latter also includes delivery modalities that employ changes in the amount of an active agent (e.g., an endothelial progenitor cell-derived exosome composition) that are delivered at different times.

In some embodiments, the sustained release formulation, the controlled release formulation, or the combination thereof is selected from the group consisting of an oral formulation, a peroral formulation, a buccal formulation, an enteral formulation, a pulmonary formulation, a rectal formulation, a vaginal formulation, a nasal formulation, a lingual formulation, a sublingual formulation, an intravenous formulation, an intraarterial formulation, an intracardial formulation, an intramuscular formulation, an intraperitoneal formulation, a transdermal formulation, an intracranial formulation, an intracutaneous formulation, a subcutaneous formulation, an aerosolized formulation, an ocular formulation, an implantable formulation, a depot injection formulation, a transdermal formulation and combinations thereof. In some embodiments, the route of administration is selected from the group consisting of oral, peroral, buccal, enteral, pulmonary, rectal, vaginal, nasal, lingual, sublingual, intravenous, intraarterial, intracardial, intramuscular, intraperitoneal, transdermal, intracranial, intracutaneous, subcutaneous, ocular, via an implant, and via a depot injection. Where applicable, continuous infusion can enhance accumulation of the endothelial progenitor cell-derived exosomes at a target site (see, e.g., U.S. Pat. No. 6,180,082). See also U.S. Pat. Nos. 3,598,122; 5,016,652; 5,935,975; 6,106,856; 6,162,459; 6,495,605; and 6,582,724. In some embodiments, the administering is via a route selected from the group consisting of intravenous and intraperitoneal.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Materials and Methods for Examples 1-8

Isolation and Characterization of Human EPC Exosomes. Human EPCs isolated from cord blood were cultured as previously described[15]. Cord blood samples were collected from umbilical veins during normal full-term, vaginal deliveries. Informed consent was obtained from the mother for all cord blood collections. This study was approved by the Institutional Review Board for Human Research at the Medical University of South Carolina, Charleston, South Carolina.

Exosomes were isolated from EPCs and control NIH3T3 cells culture medium. EPCs were cultured in endothelial basal medium (EBM-2, Lonza) supplemented with EBM-2 SingleQuots (Lonza) containing 10% exosome depleted fetal bovine serum (FBS, System Biosciences), 1% penicillin and streptomycin (Gibco) for 48 hours while NIH3T3 cells were cultured in DMEM medium (Gibco) containing 10% exosomes depleted fetal bovine serum (FBS, System Biosciences), 1% penicillin and streptomycin (Gibco) for 48 hours before exosome isolation. Medium was harvested and centrifuged at 2000×g for 30 mins to remove cells and debris. Exosomes were then isolated from the cell-free medium using the Total Exosomes Isolation Kit following the manufacturer's instructions (Invitrogen) and resuspended in PBS. The total protein concentration of the exosomes was measured by BCA assay (Bio-Rad). Isolated exosomes were diluted in PBS and measured by nanoparticle tracking analysis (NTA) with Zetaview PMX 120 (Particle Metrix, Meerbusch, Germany)[28]. The size distribution and total number of exosomes were analyzed by nanoparticle tracking analysis software (ZetaView Aug. 4,2002).

Cecal Ligation and Puncture. CD-1 mice (male, aged 7-8 wk) were housed in a germ-free environment. Investigations conformed to the Guide for the Care and Use of Laboratory Animals published by the National Institutes of Health and were approved by the Institutional Animal Care and Use Committee at the Medical University of South Carolina. CLP was performed as previously described[29]. Briefly, the cecum was ligated at the colon juncture with a 5-0 silk ligature suture without interrupting intestinal continuity and then punctured twice with a 22-gauge needle. All animals were fluid-resuscitated subcutaneously with saline. The sham operation was performed in the same way as CLP except for the ligation and puncture of the cecum.

For the survival study, mice were randomly assigned to one of four groups: sham, CLP-PBS, CLP-EPC-Exosomes and CLP-NIH3T3-Exosomes. At 4 hours after CLP surgery, mice were injected intravenously with PBS, EPC-exosomes (2 mg/kg body weight) or NIH3T3-exosomes (2 mg/kg body weight). Mice received imipenem (25 mg/kg, subcutaneously) at 6, 24, and 48 hours after CLP and survival rate was monitored for 7 days.

Organ Function Measurement and Cytokine/Chemokine Analyses. Whole blood was collected from mice of each group at 24 h after surgery and was transferred to tube containing EDTA (BD Vacutainer). Plasma was separated by centrifugation at 10,000 rpm for 30 min and stored at −80° C. for future analysis.

The plasma levels of ALT, AST, and BUN were used as indicators for liver and kidney function, respectively, and were measured using ELISA kits (BioAssay Systems).

The plasma levels of IL-6, IL-10, TNF-α, INFγ, and MCP-1 were determined by mouse cytokine array pro-inflammatory focused 10-plex, which was performed and analyzed by Eve Technologies (Calgary, Canada).

Lung and Kidney Pathology. The lung and kidney tissues were collected from mice of each in vivo group at 48 h after CLP surgery. The lung tissue was inflated with 10% buffered formalin and both lung and kidney tissues were fixed with 10% buffered formalin, embedded in paraffin and cut into 5-μm sections. Tissue sections were stained with hematoxylin and eosin (H&E) for examination of morphological damage microscopically. At least 10 random lung fields and kidney fields were examined per animal. The lung and kidney injury were evaluated and scored by a pathologist who was blinded to the experimental groups. Lung and kidney injury scores were evaluated as previously described[30].

Lung and Kidney Vascular Leakage and Lung Wet/Dry Ratio Measurement. Vascular leakage was quantified using the Evans blue dye assay in lung and kidney tissue as described previously[31]. Briefly, the mice were administered 1% Evans blue dye solution (Sigma) in saline via tail vein injection. After 40 min, the mice were sacrificed, perfused via the heart and the lung and kidney tissues were collected. The lung and kidney weight was measured and placed in 1 ml of formamide (Avantor) at 60° C. for 24 h to extract Evans blue. The samples were centrifuged at 2,000 rpm for 10 min, and the supernatant was collected. The concentration of Evans blue dye in the supernatant was quantified by measuring absorbance at 620 nm from a standard curve by a plate reader.

For lung water content, the left lung was harvested and weighed to measure a wet weight in each group. The wet lung was then dried in an oven at 60° C. for 48 h, and re-weighed as dry weight. The lung water content was calculated as the ratio of wet weight to dry weight.

MicroRNA Contents in EPC-exosomes and NIH3T3-exosomes. Total RNA was extract from 200 ul of EPC-exosomes and NIH3T3-exosomes using the RNeasy Mini Kit (Qiagen) following the manufacturer's instructions. Extracted RNA (100 ng) was used to prepare miRNA-focused next generation sequencing (NGS) libraries using QIAseq™ miRNA Library Kit (Qiagen). The sequencing was performed on an Illumina HiSeq 2500 instrument at the MUSC Genomic Sequencing Core Facility. The data analysis was performed with the QIAseq miRNA quantification platform using unique molecular index (UMI) counts according to the manufacturer's instructions.

MicroRNA Inhibitor Transfection. MiR-126-3p and 5p inhibitors and a control inhibitor were purchased from Qiagen. EPCs were cultured and then transfected with miR126-3p or 5p inhibitors (50 nM) or both (25 nM each) or negative control inhibitor (50 nM) using Hiperfect transfection reagent (Qiagen) according to the manufacturer's instruction. Culture medium was replaced with medium containing exosomes-depleted FBS (System Biosciences) at 6 h after transfection. Then the exosomes were isolated at 48 h after transfection as previously described. Isolated exosomes were administered to mice in survival studies as described above and to human microvascular endothelial cells (HMVECs) as described below.

HMVECs Culture and Treatment. HMVECs were cultured in EBM-2 (Lonza) supplemented with EGM-2 MV SingleQuot (Lonza) containing 5% fetal bovine serum and 1% penicillin/streptomycin. HMVECs were seeded at $5 \times 10^5$ cells/ml with FBS-free culture medium in 12-well plates and treated with exosomes from transfected and untransfected EPCs for 4 hours. Cells were then further stimulated with LPS (100 ng/ml) for another 24 h. The total protein was extracted from cells, and HMGB1 and VCAM1 protein levels were measured by western blot.

Real-time Reverse Transcription-PCR. Total RNA was extracted from lung tissue using miRNeasy kit (Qiagen) according to the manufacturer's instructions. For miRNA expression, the RNA (12 μl per reaction) was reverse transcribed using Qiagen miRNA Reverse Transcription Kit (Qiagen). Following cDNA synthesis, the levels of microRNA126-3p or 5p were determined by CFX96 Real-Time PCR system (Bio-Rad) using SYBR green qPCR master mix (Qiagen) according to the manufacturer's instructions. Data were analyzed with $2^{-\Delta\Delta Ct}$ value calculation, using RNU6 for normalization.

Western Blot. Cells were homogenized and lysed with ice-cold RIPA lysis buffer (Abcam) containing protease and phosphatase inhibitors (Cell Signaling). All lysed samples were kept on ice for 30 min, and centrifuged for 10 min at 4° C. at 10,000 g. The cell lysate was collected and protein concentration was measured using a BCA assay kit (Bio-Rad). Fifty μg of protein was used for western blot analysis. Primary antibodies including anti-HMGB1 (Cell Signaling, 1:1000) and anti-VCAM1 (Cell Signaling, 1:500) were used. Peroxidase labelled anti-rabbit antibody (GE healthy) was used as secondary antibody. α-tubulin (Cell Signaling, 1:1000) was used as a loading control. The immunoreactive protein bands were visualized by ECL detection kit (GE Healthcare) and analyzed using Image J software.

Statistical Analysis. All the in vitro experiments were performed at least three independent times. The data were analyzed using GraphPad Prism 7.01 software. The log-rank test was used for comparisons in the survival study while analysis of variance with the Fisher probable least-squares difference test was used for other comparisons. A value of $p<0.05$ was considered statistically significant.

Example 1

EPC-Exosomes Characterization

The isolated EPC-exosomes were characterized by nanoparticle tracking analysis with ZetaView. We isolated $3.5 \times 10^{10}$ particles (containing 0.75 mg exosome protein) from the culture medium of $2.5 \times 10^6$ cells with a concentration of $7 \times 10^{10}$ particles/ml. The average size of exosomes is 71.5 nm and more than 90% of exosomes are within 30-120 nm range (see FIG. 1), consistent with previous work[2B].

Example 2

EPC-Exosome Treatment Improved Survival in CLP-Induced Sepsis

Figure 2:
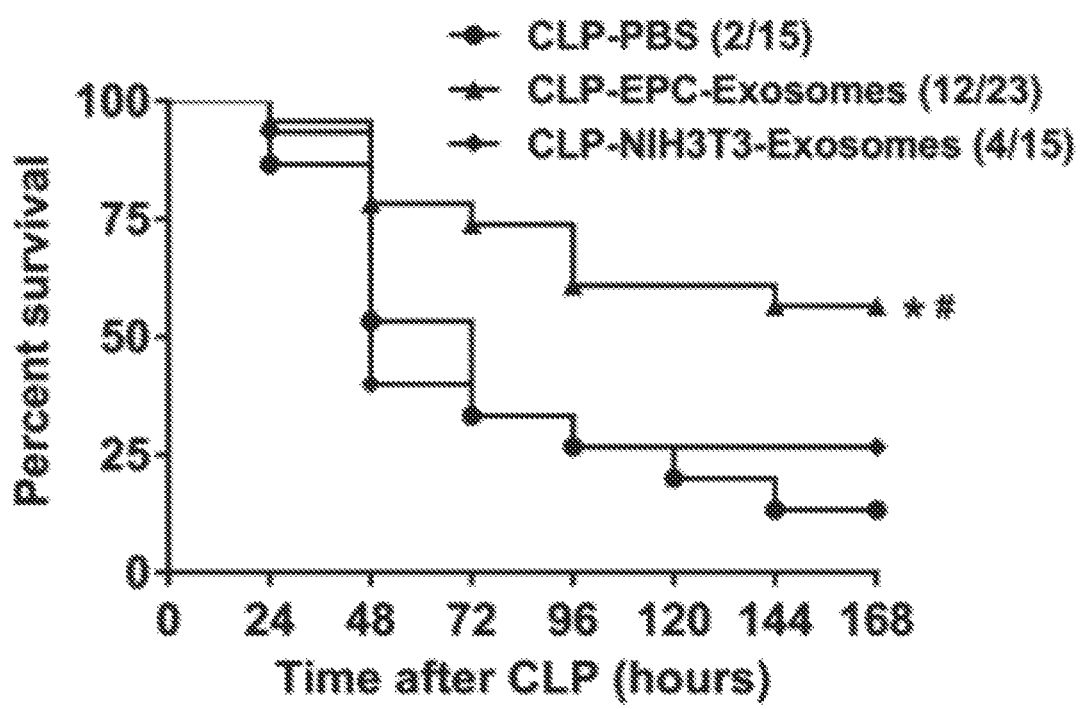
FIG. 2 is a graph of the effect of EPC-exosomes on CLP-induced mortality. CD-1 mice were subjected to CLP and treated with EPC-exosomes (2 mg protein/kg body weight; triangles), control NIH3T3-exosomes (2 mg protein/kg body weight; diamonds), or PBS (circles). Survival rate was monitored for a total of 168 hours (7 days). *$p<0.05$ compared with CLP-PBS group, #$p<0.05$ compared with CLP-NIH3T3-exosomes group. N=15-23 mice per group.

To determine whether EPC-exosomes are beneficial, septic mice were injected intravenously with either EPC exosomes (2 mg protein/kg body weight), NIH3T3-exosomes (2 mg protein/kg body weight) or PBS (control) 4 h after CLP surgery. Mouse survival was monitored for 7 days (168 hrs.). Septic mice treated with EPC-exosomes exhibited a significantly increased survival rate compared to mice treated with either NIH3T3-exosomes or PBS (52% vs. 26% and 52% vs. 13%, respectively; $p<0.05$; see FIG. 2). No significant difference in mortality was observed between NIH3T3-exosomes and PBS (26% vs. 13%; see FIG. 2).

Example 3

Figure 3A:
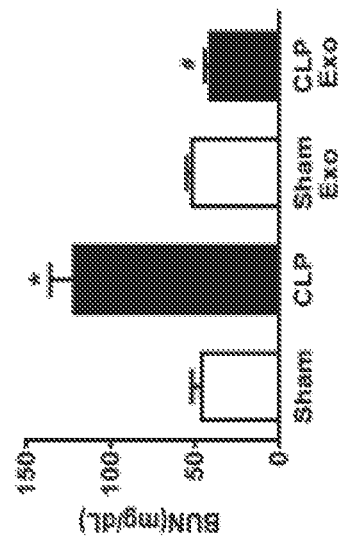
Figure 3B:
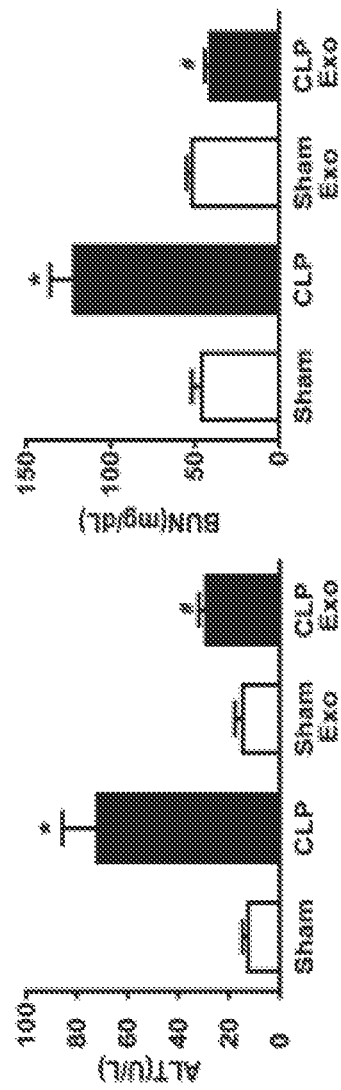
Figure 3C:
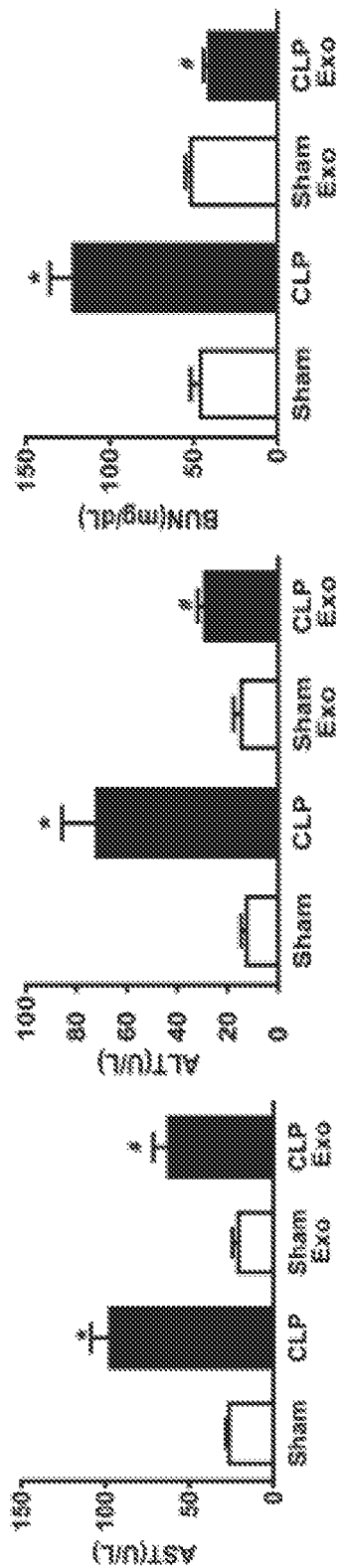

EPC-Exosomes Attenuated Organ Injury and Vascular Permeability in CLP-Induced Sepsis Multi-organ dysfunction is a major cause of death during sepsis. We determined if EPC-exosomes improve organ dysfunction in septic mice. Sepsis induced both liver and renal injury as evidenced by the increased ALT, AST and BUN levels in the plasma of septic versus control mice ($p<0.05$; see FIGS. 3A-3C). However, treatment with EPC-exosomes significantly attenuated these organ injuries ($p<0.05$; see FIGS. 3A-3C).

Figure 3D:
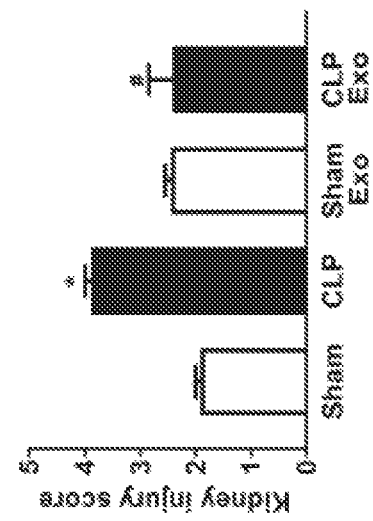
Figure 3E:
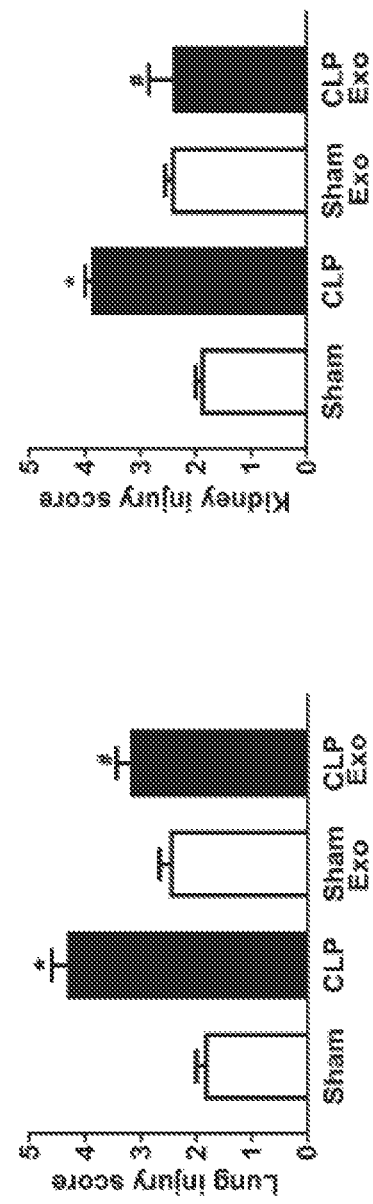
Figure 4A:
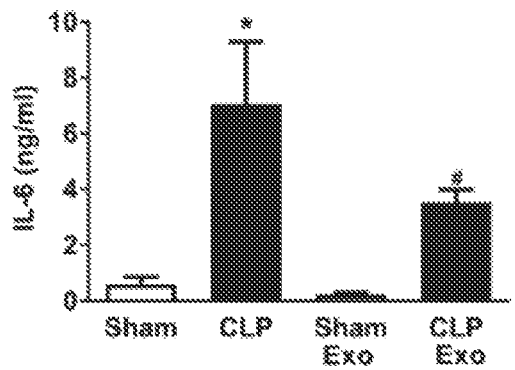
FIGS. 4A-4E are a series of bar graphs showing the effects of EPC-Exosomes on plasma cytokine/chemokine levels in septic mice. Mice were subjected to sham or CLP and injected with EPC-exosomes (2 mg protein/kg body weight) or control PBS (same volume) at 4 h after CLP surgery. Plasma cytokine IL-6 (FIG. 4A), INFγ (FIG. 4B), TNFα (FIG. 4C), IL-10 (FIG. 4D), and chemokine MCP-1 (FIG. 4E) levels were determined by mouse cytokine and chemokine array at 24 h-post CLP. *p<0.05 compared with sham group, #p<0.05 compared with CLP group. N=3-4 mice per group.
Figure 4B:
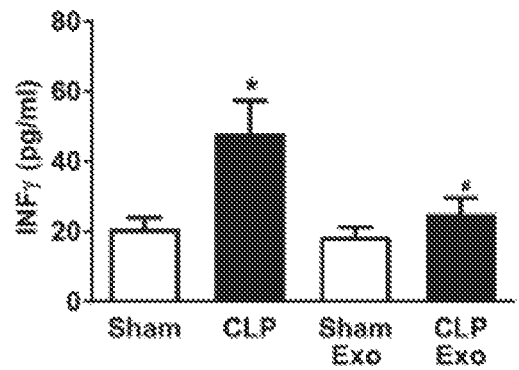
Figure 4C:
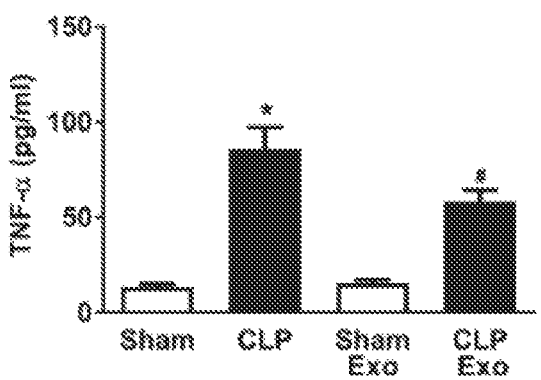
Figure 4D:
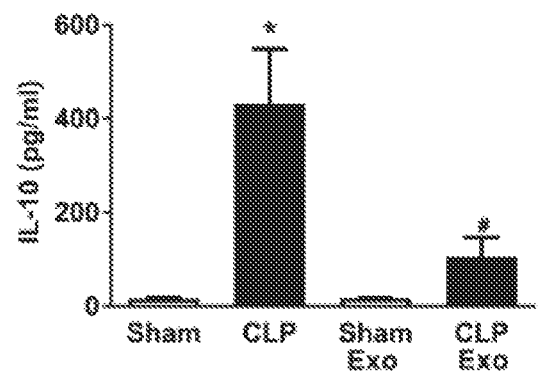
Figure 4E:
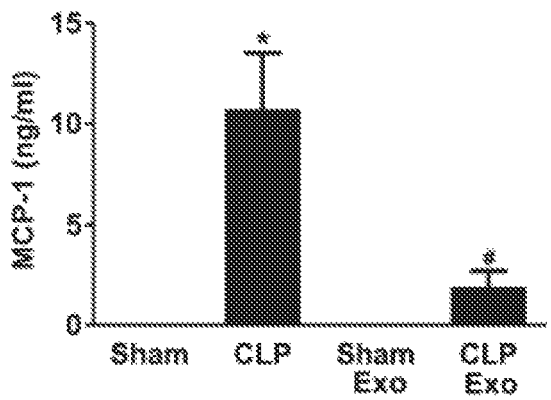

Lung and kidney sections were stained with H&E and examined histologically. The representative sections were reviewed at 400× magnification. For lung histology, infiltrated inflammatory cells were observed in the alveoli; and enlarged interstitial space was observed. For kidney histology, a shrunken glomerulus was observed, as were a tubular injury including brush border loss and tubular luminal debris or obstruction and capillary congestion. To elaborate, histologic examination of the sham group revealed normal lung morphology without the presence of infiltrating inflammatory cells. However, in the CLP group, there were increases in alveolar wall thickening, enlarged interstitial spaces and alveolar inflammatory cell infiltration consistent with lung injury. These findings were significantly reduced after treatment with EPC-exosomes. Normal kidney architecture with intact glomeruli, intact brush border of tubular cells and uniform endothelium were observed in the sham group but not in the CLP group. Treatment with EPC-exosomes ameliorated sepsis-related brush border loss, reduced tubular injury and decreased capillary congestion in the kidney of CLP-induced septic mice (see FIGS. 3D and 3E).

The effect of EPC-exosomes on vascular leakage and lung edema was further investigated. CLP mice exhibited a marked increase in lung and kidney vascular leakage, which were both reversed by EPC-exosome treatment ($p<0.05$; see FIGS. 3F and 3G). Moreover, treatment with EPC-exosomes significantly reduced lung water content compared to CLP mice ($p<0.05$; see FIG. 3H).

Example 4

EPC-Exosomes Reduced Plasma Cytokine/Chemokine Levels in CLP-Induced Sepsis

Sepsis is associated with a systemic inflammatory response driven, in part, by cytokines and chemokines. Whether treatment with EPC-exosomes had an effect on cytokine and chemokine expression levels in the plasma of septic mice. CLP significantly increased the pro-inflammatory cytokines (IL-6, INFγ, TNFα) and anti-inflammatory cytokine IL-10 as well as the chemokine MCP-1 ($p<0.05$; see FIG. 4A-4E). However, treatment with EPC-exosomes significantly attenuated these increases ($p<0.05$; see FIG. 4A-4E).

Example 5

MiR-126-3P and 5P are Abundantly Expressed in EPC Exosomes

Figure 5A:
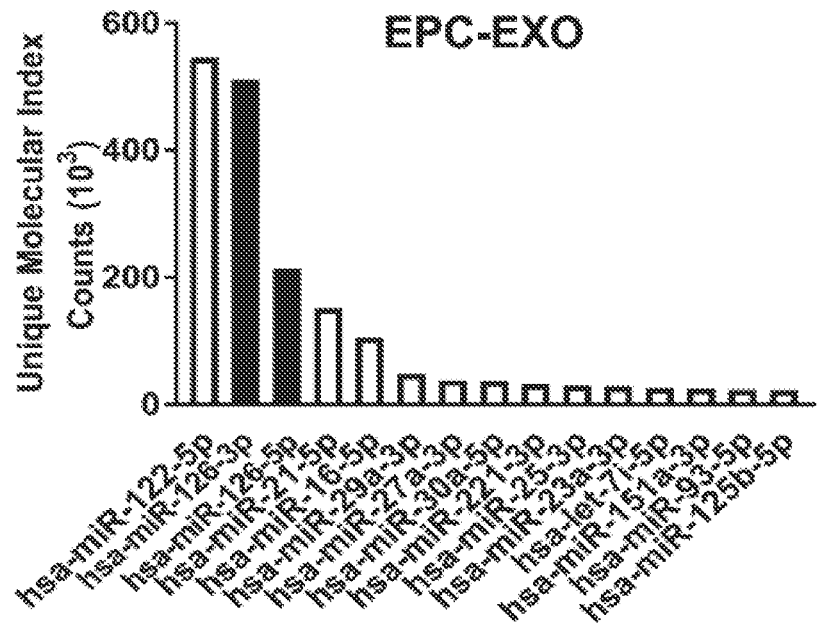
FIGS. 5A and 5B are bar graphs showing that highly expressed microRNAs differed between EPC-exosomes and NIH3T3 exosomes. MicroRNA content in EPC-exosomes (FIG. 5A) and NIH3T3 cell exosomes (FIG. 5B) were analyzed by Next-generation sequencing. Each microRNA expression level was determined by Unique molecular index (UMI) from three independent experiments.
Figure 5B:
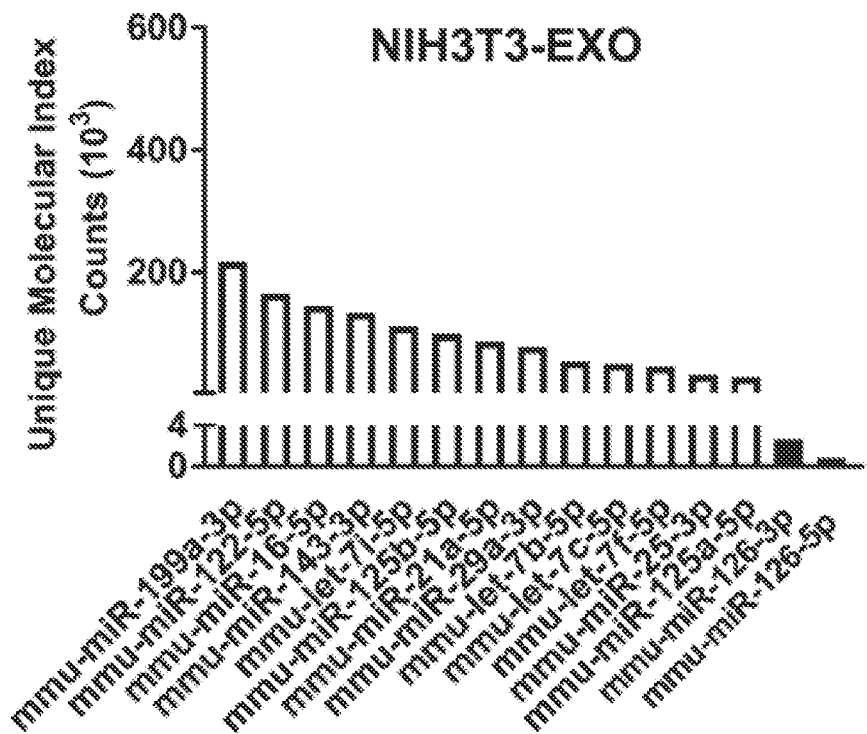

The microRNA contents of EPC and NIH3T3 cell exosomes were analyzed and compared by precision next generation sequencing. Although miR-122-5p was highly expressed in the exosomes from both cells, miR-126-3p and 5p were highly abundant in EPC-exosomes and not in the NIH3T3-exosomes (see FIGS. 5A and 5B). In combination with the known protective effects of miR-126 on vascular integrity[32-34], this observation led to further investigation of the potential roles of miR-126-3p and 5p in sepsis.

Example 6

Treatment with EPC-Exosomes Increased miR-126 Expression in Lung Tissue

Figures 6A, 6B:
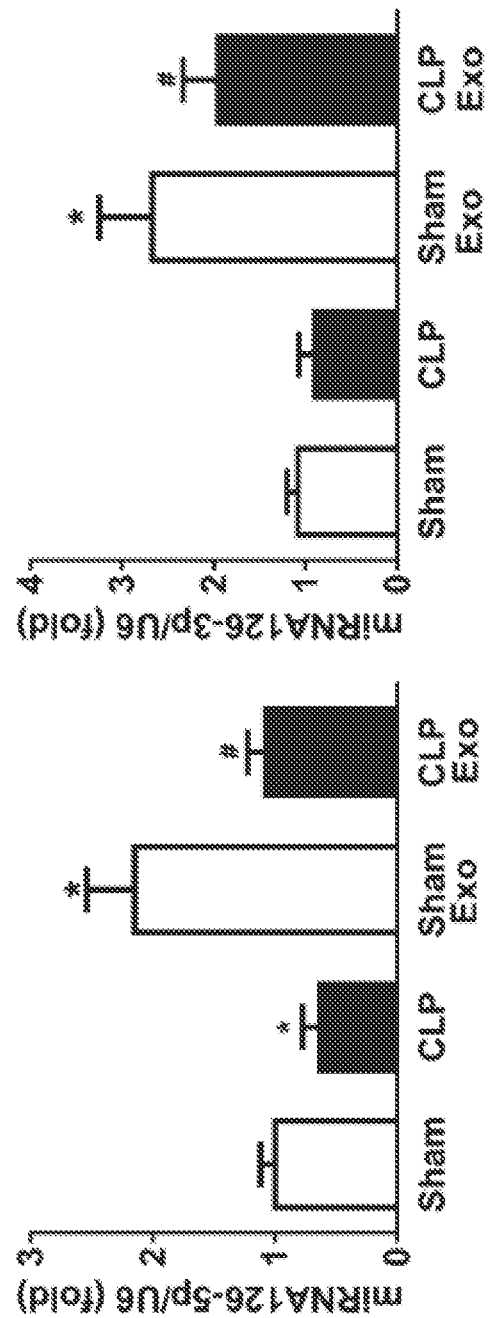
FIGS. 6A and 6B are bar graphs showing the effects of EPC-exosomes on miRNA-126-5p and 3p expression in lung tissue in CLP-induced sepsis. Lung miRNA-126-5p (FIG. 6A) and -3p (FIG. 6B) expression was determined by real-time qPCR. *p<0.05 compared with sham group, #p<0.05 compared with CLP group. N=3-6 mice per group.

As miR-126-3p and 5p are abundant in EPC-exosomes, whether their administration could increase miR-126-3p and 5p expression in the mouse lung was investigated using RT-PCR. Whole lung homogenate was examined 24 hours post-surgery. In both sham-operated and CLP-septic mice, treatment with EPC-exosomes significantly augmented miR-126-3p and 5p expression levels compared to untreated mice (see FIGS. 6A and 6B).

Example 7

EPC-Exosomes Suppressed LPS-Response in HMVECs Through the Delivery of miR-126

Figure 7A:
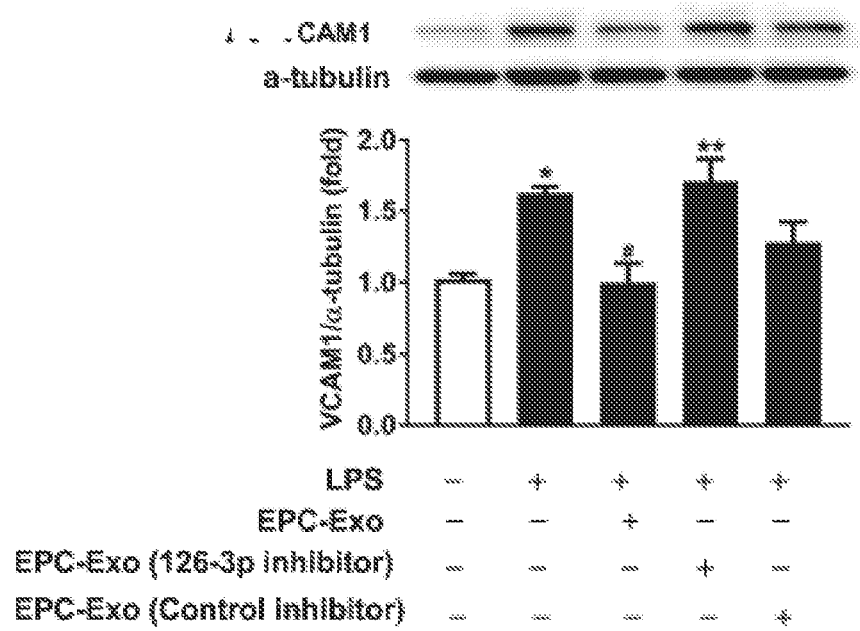
FIGS. 7A-7C are a series of graphs showing the effects of EPC exosomal miR-126-3p and 5p on LPS-induced HMVEC target expression and CLP-induced mortality. Protein level of HMGB1 (FIG. 7A) and VCAM1 (FIG. 7B) in HMVECs were measured by western blot. α-tubulin served as an internal control. *p<0.05 compare with control group, #p<0.05 compare with LPS group, **p<0.05 compare with LPS+ EPC-exosomes group. The results represent the means±SE of three independent experiments. CD-1 mice were subjected to CLP and treated with EPC exosomes, miR-126-reduced EPC exosomes (2 mg protein/kg body weight), or PBS. Survival rate was monitored for a total of 168 hr (7 days) (C). n=15-16 mice per group.
Figure 7B:
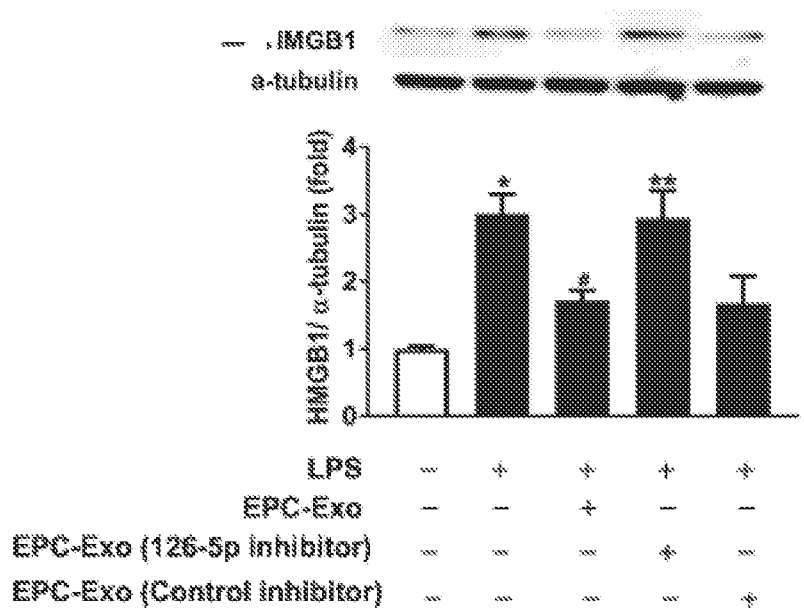

The potential mechanism of the beneficial effects of EPC exosomal microRNA-126-3p and 5p was examined by measuring the expression of their targets with established relevance to sepsis, VCAM1 and HMGB1, respectively. Lipopolysaccharide increased the protein expression of VCAM1 and HMGB1 in HMVECs while co-treatment with EPC-exosomes mitigated these effects (see FIGS. 7A and 7B). Moreover, reduction of exosomal miR-126-3p and 5p content through transfection of EPCs with their inhibitors abrogated these reductions of VCAM1 and HMGB1, respectively (see FIGS. 7A and 7B). Thus, EPC-exosomes suppressed LPS-induced increases in VCAM1 and HMGB1 protein levels via miR-126-3p and 5p.

Example 8 miRNA-126-Depleted EPC-Exosomes No Longer Improve Sepsis Survival

Figure 7C:
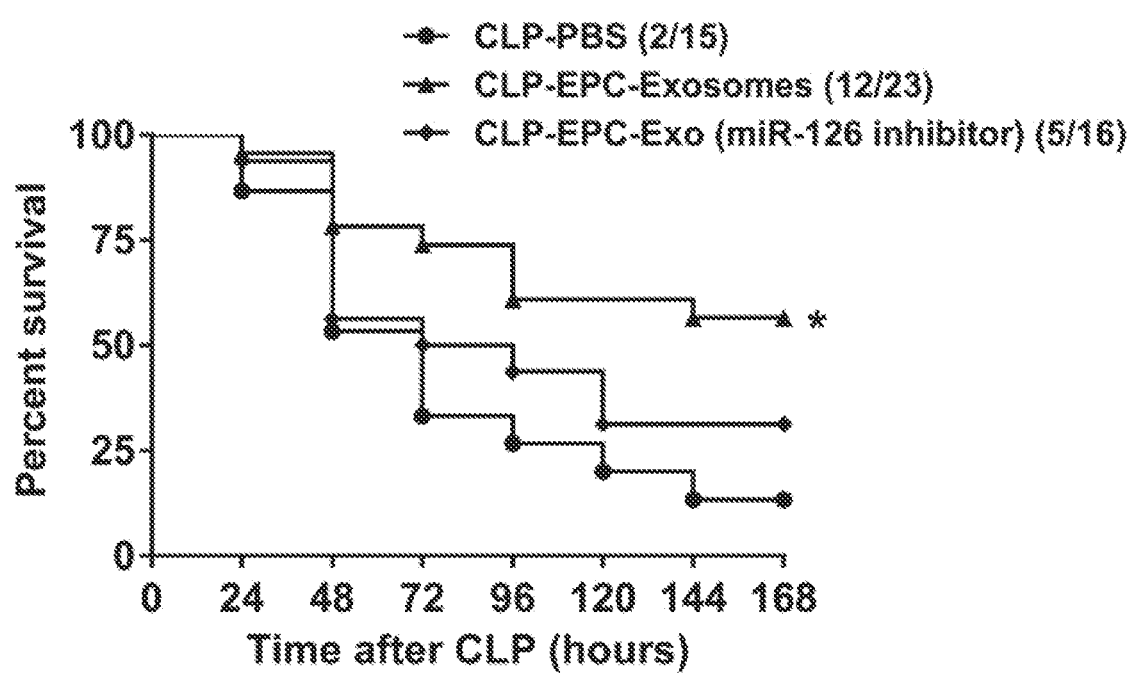

The potential role of exosomal miR-126 in the survival benefit of EPC-exosomes in CLP-induced sepsis was investigated. EPC exosome treatment significantly enhanced survival compared with the PBS group (FIG. 7C). The group was shown here again for comparison. However, septic mice treated with miR-126-3p and 5p-depleted EPC-exosomes exhibited no significant difference in survival compared to mice treated with PBS (see FIG. 7C). This suggests that the beneficial effects of EPC-exosomes in sepsis are mediated through the delivery of miR-126.

Example 9

Treatment of Ards in a Murine Model

In this Example, to determine if EPC exosomes would have beneficial effects in ALI, intratracheal administration of lipopolysaccharide (LPS) was used to induce ALI in mice. Lung permeability, inflammation, and the role of miRNA-126 in alveolar epithelial barrier function were examined. The intratracheal administration of EPC exosomes reduced lung injury following LPS-induced ALI at 24 and 48 hours. Compared to placebo, intratracheal administration of EPC exosomes significantly reduced the cell number, protein concentration and cytokines/chemokines in the bronchoalveolar lavage fluid (BALF), indicating a reduction in permeability and inflammation. Further, EPC exosomes reduced myeloperoxidase (MPO) activity, lung injury score and pulmonary edema, demonstrating protection against lung injury. Murine fibroblast (NIH3T3) exosomes, which do not contain abundant miRNA-126, did not provide these beneficial effects. In human small airway epithelial cells (SAECs), it was found that overexpression of miRNA-126-3p can target phosphoinositide-3-kinase regulatory subunit 2 (PIK3R2), while overexpression of miRNA-126-5p inhibits the inflammatory alarmin HMGB1 and permeability factor VEGFα. Interestingly, both miR-126-3p and 5p increase the expression of tight junction proteins suggesting a potential mechanism by which miRNA-126 may mitigate LPS-induced lung injury. Thus, these data demonstrated that human EPC exosomes are beneficial in LPS-induced ALI mice, in part through the delivery of miRNA-126 into the injured alveolus.

Materials and Methods for Example 9

Isolation and characterization of exosomes. This study was approved by the Institutional Review Board for Human Research at the Medical University of South Carolina. Human EPCs were isolated from cord blood from healthy pregnant woman and were cultured as previously described (Fan H, et al., *American journal of respiratory and critical care medicine* 2014). Briefly, cord blood samples were collected from umbilical veins during normal full-term, vaginal deliveries and informed consent was obtained from the mother for all cord blood collections. EPCs were cultured in endothelial basal medium (EBM-2; Lonza, Allendale, NJ, USA) supplemented with EBM-2 SingleQuots (Lonza, Allendale, NJ, USA) containing 10% exosome-depleted fetal bovine serum (FBS; System Biosciences, Palo Alto, CA, USA), 1% penicillin and streptomycin (GIBCO, Gaithersburg, MD, USA) for 48 h, while NIH3T3 cells were cultured in Dulbecco's Modified Eagle's medium (DMEM, GIBCO, Gaithersburg, MD, USA) containing 10% exosome-depleted FBS (System Biosciences, Palo Alto, CA, USA), 1% penicillin and streptomycin (GIBCO, Gaithersburg, MD, USA) for 48 h. Medium was harvested and centrifuged at 2,000×g for 30 min to remove cells and debris. Exosomes were then isolated from the cell-free medium using the Total Exosomes Isolation Kit following the manufacturer's instructions (Invitrogen, Asheville, NC, USA) and re-suspended in PBS.

The total protein concentration of the exosomes was measured by detergent-compatible (DC) protein assay (Bio-Rad, Hercules, CA, USA). The size distribution and total number of exosomes were analyzed by nanoparticle tracking analysis (NTA) with ZetaView PMX 120 (Particle Metrix, Meerbusch, Germany). Exosome markers, such as tetraspanin proteins CD9, CD63 and CD81, were determined by western blot. Each experiment was carried out in triplicate.

Lipopolysaccharide-induced acute lung injury model. Elsewhere herein it is shown that EPC exosomes exert protective effects in a cecal ligation and puncture model, which is a clinical relevant murine model of sepsis. To explore the effects of EPC exosomes in a murine ALI model, intratracheal instillation of LPS was used to induce ALI. Investigations conformed to the Guide for the Care and Use of Laboratory Animals published by the NIH and were approved by the Institutional Animal Care and Use Committee at the Medical University of South Carolina. CD-1 outbred mice (aged 7-8 weeks) were housed in a pathogen-free environment. The mice underwent intratracheal instillation of either 25 µg LPS diluted in 75 µl PBS as described previously (Guo C, et al., *Mol Med* 2016) or 75 µl PBS. Four hours after acute lung injury induction, the mice were treated with 70 µg of EPC-exosomes or negative control NIH3T3-exosomes or PBS separately through intratracheal administration. Thus, 4 experimental groups were created: 1) PBS control, 2) LPS+PBS, 3) LPS+EPC-exo and 4) LPS+3T3-exo. Subsequent experiments examined 3 to 7 mice per group. Bronchoalveolar lavage fluid fluid (BALF) and perfused lung tissues for myeloperoxidase (MPO) activity and Evans blue assay were collected at 24 h as described below and formalin-fixed paraffin-embedded histological lung tissues were collected at 48 h after lung injury. All the samples were stored at −80° C. or 4° C. until analysis.

Assessment of Lung Inflammation. Lung inflammation was compared between experimental groups using the following methods: 1) measurement of BALF cell count, 2) measurement of BALF cytokines and chemokines, and 3) measurement of lung tissue myeloperoxidase activity. BALF was collected from mice in each group 24 hours after LPS instillation. After euthanasia, the thorax was opened to expose the trachea. The trachea was cannulated with a 20 g_angiocatheter and lavaged four times with cold PBS (0.75 mL) using a 1-mL syringe. The BALF was centrifuged at 600×g for 5 min to pellet cells. The cell pellet was resuspended in 500 µL red blood cell lysis buffer and centrifuged at 600×g for 5 min. Cell pellets were re-suspended in 500 µL PBS, and immune cells were quantified using a Countess II automated cell counter (Thermo Fisher Scientific, Waltham, MA, USA). The supernatant was collected and analyzed for cytokine and chemokine levels using the pro-inflammatory focused 32-plex (Eve Technologies, Calgary, AB). The remaining supernatant was aliquoted and frozen at −80° C. for additional experiments.

Myeloperoxidase activity was determined in lung tissue as an index of neutrophil accumulation as previously described (Pulli B, Ali M, et al., *PLoS One* 2013; 8: e67976; Fan H, et al., *Am J Physiol Cell Physiol* 2005; 289: C293-301. Briefly, lung tissues were perfused, weighed and homogenized in 1 ml potassium phosphate buffer (50 Mm, PH 6.0). The homogenized tissues were centrifuged for 15 min at 10000 rpm and the supernatant was discarded. The tissues were re-suspended in 1 ml potassium phosphate solution (50 mM) containing 0.5% hexadecyl-trimethylammonium and sonicated for 20 seconds. Samples were frozen and thawed twice and centrifuged for 10 min at 10000 rpm. The supernatants (10 µl) were combined with 80 µl 0.75 mM $H_2O_2$ (Sigma, St. Louis, MO, USA) and 110 µl TMB solution (2.9 mM TMB in 14.5% DMSO and 150 mM sodium phosphate buffer at pH 5.4), and the plate was incubated at 37° C. for 5 min. The reaction was stopped by adding 50 µl $H_2SO_4$ (2M, Sigma, St. Louis, MO, USA), and the absorption was measured at 450 nm. The quantification of MPO was calculated from a MPO standard curve and was expressed in units per g of the tissue.

Measurement of Lung Vascular Leak. Lung vascular leak was measured in each experimental group using: 1) Evan's blue assay in lung and kidney tissue, 2) lung water content, and 3) BALF protein concentrations. The Evans blue dye assay was performed as described previously (Radu M, Chemoff J., *J Vis Exp* 2013: e50062). Briefly, the mice were administered 1% Evans blue dye solution (Sigma, St. Louis, MO, USA) in saline via tail vein injection. After 40 min, the mice were sacrificed, perfused via the heart and the lung tissues were collected. The lung weights were measured and placed in 1 ml of formamide (Avantor, Center Valley, PA, USA) at 60° C. for 24 h to extract Evans blue dye. The samples were centrifuged at 2,000 rpm for 10 min, and the supernatants were collected. The concentrations of Evans blue dye in the supernatants were quantified by measuring absorbance at 620 nm and calculated from a standard curve by a plate reader.

For lung water content, the left lung was harvested and weighed to measure a wet weight in each group. The wet lung was then dried in an oven at 60° C. for 48 h and re-weighed as dry weight. The lung water content was calculated as the ratio of wet weight to dry weight. Protein levels in the BALF supernatant were determined by DC protein assay (Bio Rad, Hercules, CA, USA).

Lung histology and lung injury score. The lung tissues were collected from mice at 48 h after LPS instillation. The lungs were inflated with 10% buffered formalin, fixed with 10% buffered formalin, embedded in paraffin, and cut into 5-µm sections. Tissue sections were stained with Haemotoxylin and Eosin (H&E), evaluated and scored by a pathologist who was blinded to the experimental groups. To evaluate the lung jury, seven independent random lung fields were evaluated per mouse for: neutrophils in alveolar spaces, neutrophils in the interstitial spaces, hyaline membranes, proteinaceous debris filling the airspaces, and alveolar septal thickening and weighted according to the relevance ascribed by the official American Thoracic Society workshop report on features and measurements of experimental acute lung injury in animals (Matute-Bello G, et al, *Am J Respir Cell Mol Biol* 2011; 44: 725-738). The resulting injury score is a continuous value between 0 and 1.

Human small airway epithelial cell (SAEC) culture and miR-126 transfection. To determine the potential effects of exosomal miR-126 on epithelial gene expression, SAECs were transfected with synthetic miR-126. SAECs were cultured in human collagen type IV-coated flasks (Sigma, St. Louis, MO) supplemented with SAGM Bullet kit culture medium (Lonza, Allendale, NJ, USA). Cells were seeded into 12-well plates and then transfected with a miR-126-3p mimic (40 nM), miR-126-5p mimic (40 nM) or control miRNA (40 nM) respectively for 48 h using human airway epithelial cell avalanche transfection reagent according to the manufacturer's instructions.

At 24 h after transfection, the cells were then stimulated with LPS (100 ng/ml; Sigma, St. Louis, MO, USA) for 24 h. The total RNA was extracted from cells, which was used to do RNA sequencing analysis as well as measurement of mRNA levels by real-time polymerase chain reaction (RT-PCR) described below.

RNA sequencing and pathway analysis. To determine the effect of miR-126-3p and -5p on gene expression profile in SAECs, we transfected SAECs with miR-126-3p, -5p or control siRNAs for 48 hours and total RNAs were isolated using RNeasy plus kit (QIAGEN, Germantown, MD, USA) following the manufacturer's instructions. Extracted RNA was used to prepare next generation sequencing (NGS) libraries and the sequencing was performed on an Illumina HiSeq 2500 instrument at the MUSC Genomic Sequencing Core Facility or by Novogene (Chula Vista, CA, USA). The pathway analysis was performed with the Genomic Sequencing Core Facility.

Real-time-PCR. Total RNA extracted from SAECs was also used to perform RT-PCR to validate differentially expressed mRNA identified in the RNAseq analysis. The RNA (10 µL per-reaction) was reverse transcribed using the High Capacity cDNA Reverse Transcription Kits (Thermo Fisher Scientific, Waltham, MA, USA). Following cDNA synthesis, the levels of mRNA were determined by CFX96 Real-Time PCR system (Bio-Rad, Hercules, CA, USA) using SYBR green qPCR master mix (QIAGEN, Germantown, MD, USA) according to the manufacturer's instructions. Data were analyzed with $2^{-\Delta\Delta Ct}$ value calculation, using GAPDH for normalization.

Western blot. EPC-exosomes and NIH3T3-exosomes were lysed with ice cold radioimmunoprecipitation assay (RIPA) lysis buffer (Abcam, Cambridge, MA, USA) containing protease and phosphatase inhibitors (Cell Signaling, Boston, MA, USA). All lysed samples were kept on ice for 30 min and centrifuged for 10 min at 4° C. at 10,000×g. The cell lysates were collected and protein concentrations were measured using a DC protein assay (Bio-Rad, Hercules, CA, USA). Approximately 20 µg of exosomes protein were loaded into each lane for western blot. All exosome specific primary antibodies including anti-CD9, anti-CD63 and anti-CD81 (System Biosciences, Palo Alto, CA, USA) were used at 1:1000 dilution and exosomes validated peroxidase-labeled secondary antibody was at 1:20000 dilution. The immunoreactive protein bands were visualized by ECL detection kit (GE Healthcare, Pittsburgh, PA, USA) and analyzed using ImageJ software.

Statistical analysis. The in vitro experiments were performed at least three independent times. The data were analyzed using GraphPad Prism 7.01 software and represented as mean±SE. Means of multiple groups were compared by one-way analysis of variance (ANOVA). Independent-sample t test were performed to compare means between two different groups. A value of $p<0.05$ was considered statistically significant.

Results of Example 9

Figures 8A, 8B, 8C:
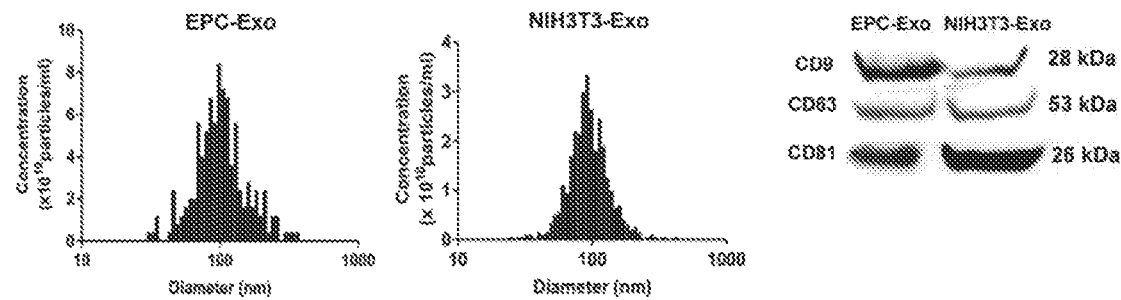
FIGS. 8A-8C show characterization of exosomes derived from human EPCs and NIH3T3 fibroblasts.

Characterization of exosomes. Nanoparticle tracking analysis (NTA) showed that the concentration of isolated EPC-exosomes is about $1.7 \times 10^{11}$ particles/ml and NIH3T3-exosomes is about $4.7 \times 10^{10}$ particles/mL. Both types of exosomes showed a similar size distribution profile with 97% of isolated particles within the 30-120 nm range (FIGS. 8A-8B). Western blot further confirmed that tetraspanin proteins (CD9, CD63, CD81) were present in all samples (FIG. 8C). These characterization data are consistent with successful exosome isolation as previously described (Helwa I, et al., *PLoS One* 2017; 12: e017062).

Figures 9A, 9B:
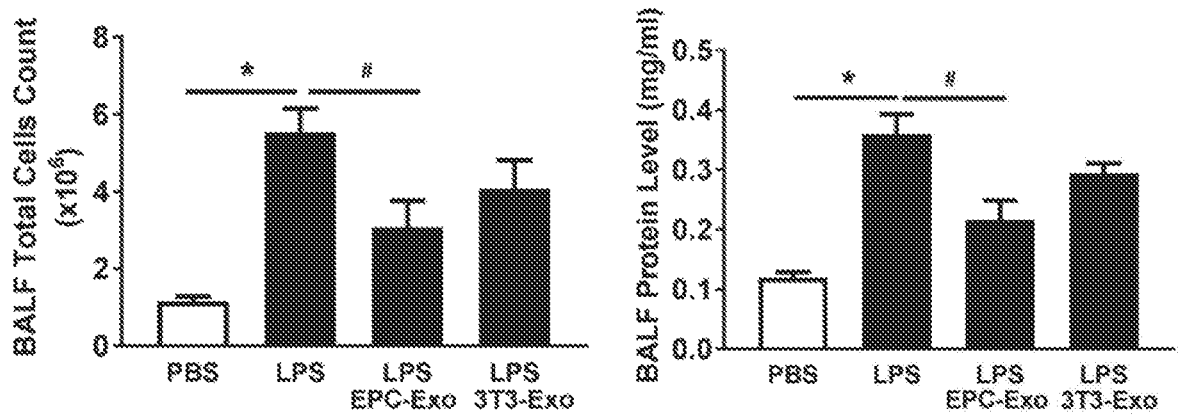
FIGS. 9A-9B are bar graphs showing therapeutic effect of EPC exosomes on bronchoalveolar lavage fluid (BALF) cell counts and protein concentration in LPS-induced acute lung injury. Mice were subjected to acute lung injury (ALI) by LPS instillation and treated with either EPC exosomes or NIH3T3 exosomes or PBS at 4 h after injury. BALF total cell counts (FIG. 9A) and BALF protein concentration (FIG. 9B) were determined at 24 h after injury. *p<0.05 compared with PBS group; #p<0.05 compared with LPS group. n=6-7 mice per group. Results are represented as mean±SE.
Figure 10:
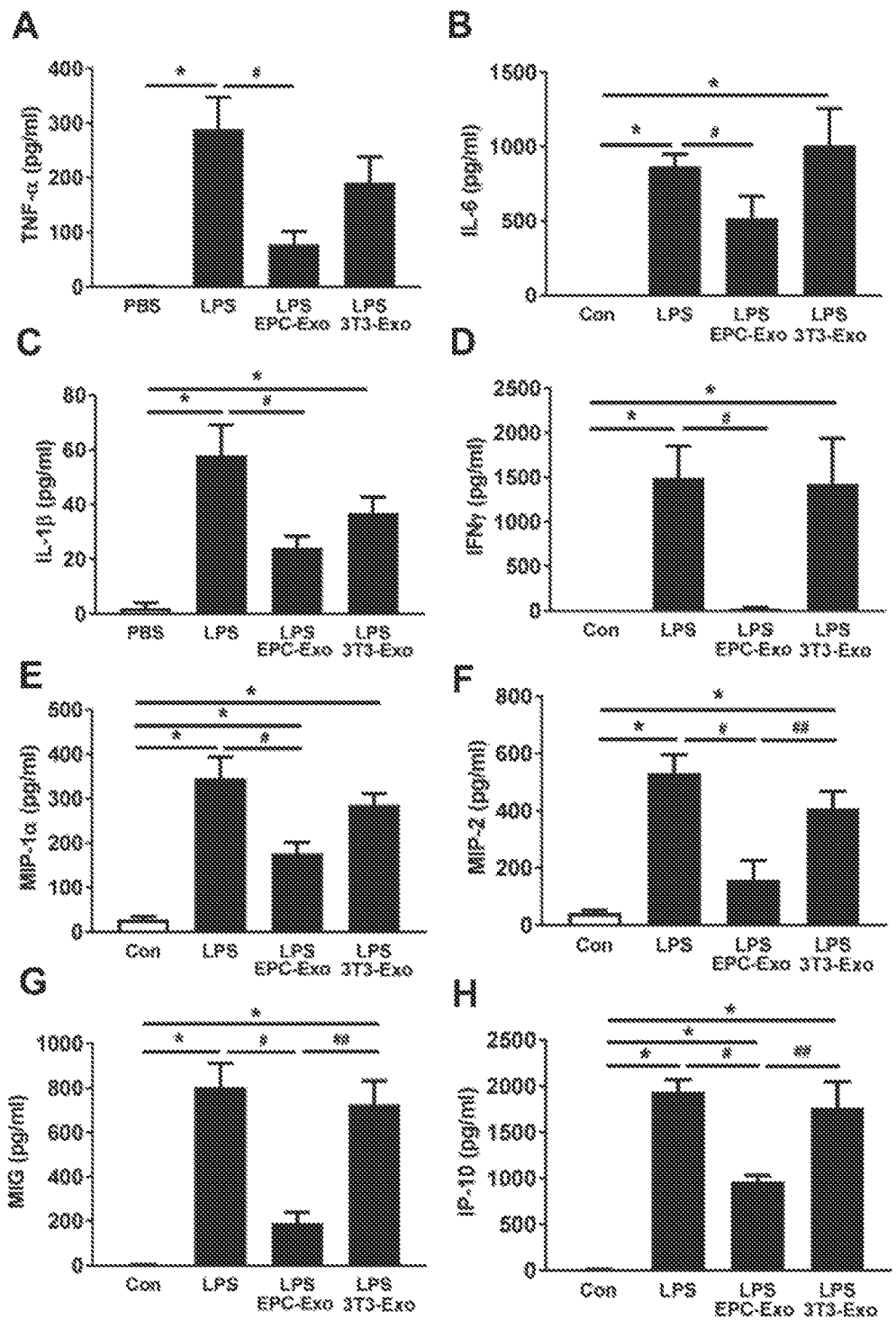
FIGS. 10A-10H are bar graphs showing therapeutic effect of EPC exosomes on BALF cytokines and chemokines in LPS induced acute lung injury. BALF cytokines TNF-α (FIG. 10A), IL-6 (FIG. 10B), IL-1β (FIG. 10C), IFNγ (FIG. 10D) and chemokines MIP-1 (FIG. 10E), MIP-2 (FIG. 10F), MIG (FIG. 10G) and IP-10 (FIG. 10H) were determined by mouse cytokine and chemokines array at 24 h after LPS installation. *p<0.05 compared with PBS group; #p<0.05 compared with LPS group. ##p<0.05 compared with LPS+ EPC-exosomes group. n=4 mice per group. Results are represented as mean±SE.

EPC exosomes decreased cells counts, protein concentration and cytokines/chemokines of BALF in LPS-induced acute lung injury. Increased BALF cell number and protein concentration are representative of ugmented endothelial and epithelial permeability. CD-1 mice underwent intratracheal instillation of LPS and were treated intratracheally with EPC exosomes or NIH3T3 exosomes at 4 h post injury. The cell counts and protein concentration levels in the BALF were determined. LPS installation significantly increased total cell counts and protein concentration level in BALF compared with PBS instillation. These effects were mitigated by intratracheal administration of EPC exosomes ($p<0.05$) but not by administration of NIH3T3 exosomes (FIG. 9A-9B).

Moreover, LPS also induced lung inflammation as evidenced by increased cytokines and chemokines including tumor necrosis factor (TNF)-α, interleukin (IL)-6, IL-1β, interferon (IFN)γ, macrophage inflammatory proteins (MIP)-1, MIP2, monokine induced by gamma interferon (MIG) and interferon gamma-induced protein (IP)-10 in the BALF compared to PBS group. EPC exosome treatment significantly attenuated these increases of inflammatory mediators ($p<0.05$; FIGS. 10A-10H), while administration of negative control NIH3T3 exosomes at the same dose had no beneficial effects in LPS-induced cytokine and chemokine production ($p>0.05$; FIG. 10A-10H). These data suggest that EPC exosome treatment reduced the damage to the alveolar capillary barrier and cytokine and chemokine release caused by LPS.

Figure 11A:
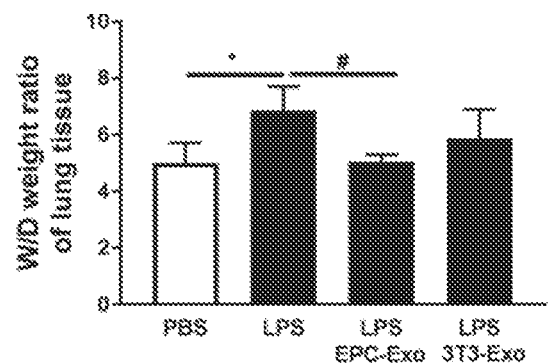
FIGS. 11A-11B are bar graphs showing therapeutic effect of EPC exosomes on alveolar edema in LPS induced acute lung injury. Lung water content was calculated as the ratio of wet weight to dry weight (FIG. 11A) and vascular leakage in lung tissue was measured via injecting Evans blue dye at 24 h after LPS instillation (FIG. 11B). *p<0.05 compared with PBS group; #p<0.05 compared with LPS group. n=4-6 mice per group. Results are represented as mean±SE.
Figure 11B:
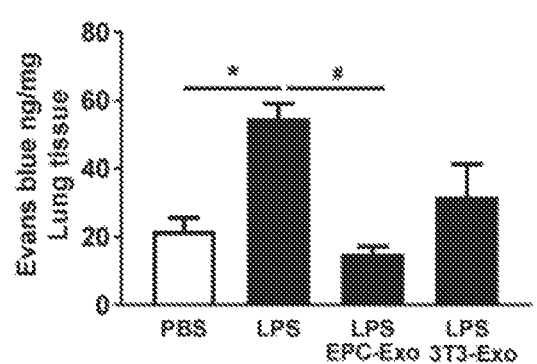

EPC exosomes reduced alveolar edema, lung injury and lung neutrophil infiltration in ALI mice. We subsequently investigated the effect of EPC exosomes on epithelial barrier integrity and alveolar edema. Lung water content expressed as wet/dry weight was significantly increased in ALI mice, which was decreased by EPC exosome treatment ($p<0.05$, FIG. 11A). Evans blue dye was used to determine changes in alveolar permeability. Mice with ALI exhibited a marked increase in alveolar edema assessed by Evans blue tissue dispersion, which was reversed by EPC exosome treatment ($p<0.05$; FIG. 11B). Histologic examination of the PBS group revealed normal mouse lung characterized by thin alveolar walls with occasional alveolar macrophages and rare neutrophils. However, the mice treated with LPS demonstrated significantly increased neutrophils in both the alveolar and interstitial spaces, hyaline membrane formation, and thickening of the alveolar walls. Lung sections were stained with H&E and examined histologically at 48 h after LPS instillation. The representative sections were viewed at ×400 original magnification, and scale bars are 20 mm. The PBS group showed normal lung tissue including thin alveolar walls and few alveolar macrophages.

Figure 12A:
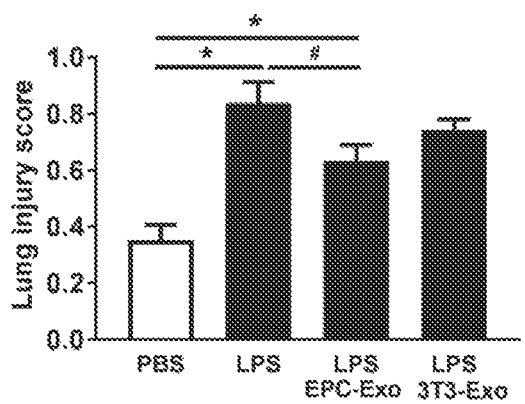
FIGS. 12A and 12B show therapeutic effect of EPC exosomes on LPS-induced acute lung injury by myeloperoxidase (MPO) activity. Lung injury scores (FIG. 12A) were assessed. *p<0.05 compared with PBS group; #p<0.05 compared with LPS group. n=4 mice per group. Results are represented as mean±SE. MPO activity (FIG. 12B in the lung tissue were measured at 24 h after LPS instillation. *p<0.05 compared with PBS group; #p<0.05 compared with LPS group. n=3-6 mice per group. Results are represented as mean±SE.
Figure 12B:
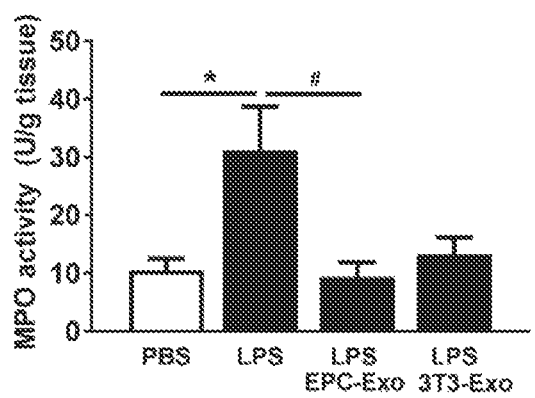
Figure 13:
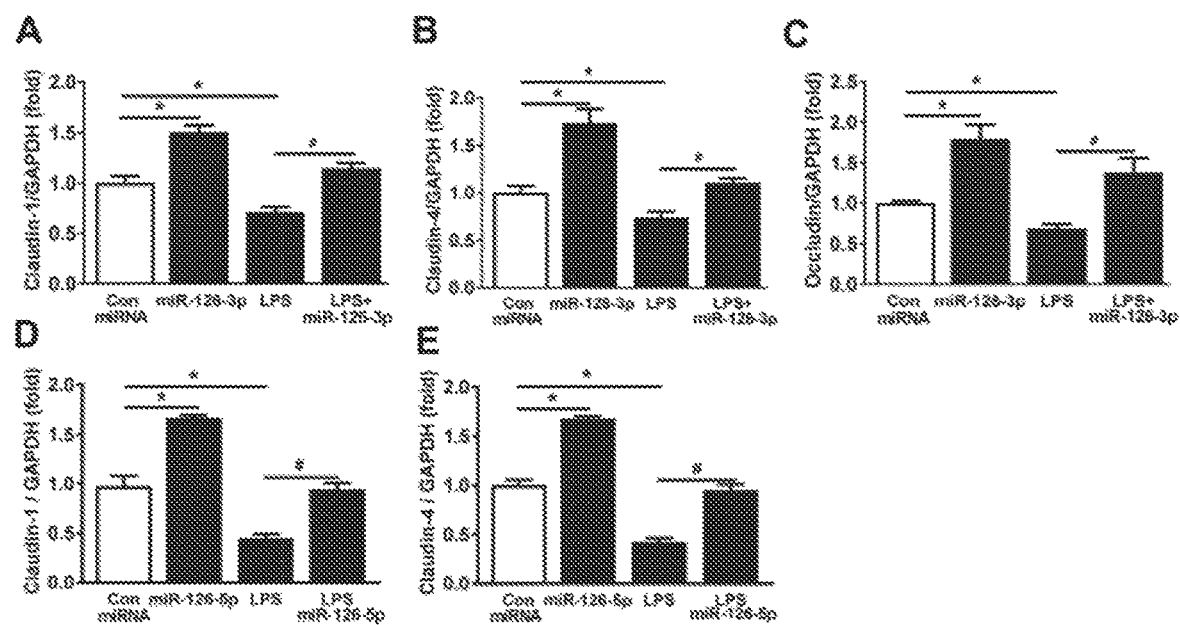
FIGS. 13A-13E are bar graphs showing that miRNA-126-3p and 5p regulate the expression levels of cell tight junction proteins in LPS-stimulated SAECs. SAECs were transfected with either miR126-3p mimic, -5p mimic or control miRNA for 48 h and stimulated with LPS (100 ng/ml) for 24 h. mRNA levels of claudin1 (FIG. 13A, FIG. 13D), claudin4 (FIG. 13B, FIG. 13E) and occludin (FIG. 13C) in SAECs were measured by RT-qPCR. GAPDH served as an internal control. *p<0.05 compared with control group; #p<0.05 compared with LPS group. The experiments were performed at least three independent times. Results are represented as mean±SE.

These observations were significantly reduced after treatment with EPC exosomes; whereas, treatment with NIH3T3 exosomes had no effect. These observations were confirmed by lung injury score evaluation ($p<0.05$; FIG. 12A) and suggested that intratracheal administration of EPC exosomes protect against lung injury while NIH3T3 exosomes do not. We also examined myeloperoxidase (MPO) activity to evaluate neutrophil accumulation in the lung tissue. LPS administration significantly increased MPO activity; whereas MPO activity was significantly reduced by EPC exosome treatment ($p<0.05$; FIG. 12B).

MIR-126-3p and 5p augmented tight junction protein levels in lung SAECs. As miR-126-3p and 5p are highly abundant in EPC exosomes but not in NIH3T3 exosomes (Zhou Y, et al., *Mol Ther* 2018; 26: 1375-1384), we examined how miR-126-3p and -5p regulate lung alveolar epithelial genes expression by RNA sequencing. SAECs were transfected with either control miRNA, miR-126-3p mimic or -5p mimic for 48 h and total RNA was isolated for RNA sequencing analysis. The RNA sequencing results showed more than 4500 genes were significantly altered by overexpression of miR-126-3p and more than 6000 genes regulated by miR-126-5p in SAECs. Pathway analysis showed that cell adhesion molecules were significantly regulated by both miR-126-3p and 5p. MiR-126-3p transfection significantly decreased PIK3R2 mRNA levels, which is a known target of miR-126-3p (22)(Table 1). MiR-126-5p similarly significantly decreased its targets high-mobility group protein (HMGB)1 and vascular endothelial growth factor (VEGF)α (Table 2). These results suggested that SAECs were successfully transfected with miR-126-3p or 5p. Moreover, the sequencing data showed that mRNA expression levels of several tight junction genes including claudin1 and claudin4 were significantly increased by both miRNA-126-3p and 5p (Table 1, 2); while occludin levels were increased by miR-126-3p (Table 1). Further, these data were validated by the RT-qPCR ($p<0.05$).

TABLE 1

SAEC genes regulated by miR-126-3p with relevance to lung barrier integrity by RNA sequencing analysis.

| Category | Gene | Fold Change | p value |
|---|---|---|---|
| Epithelial tight junction | Claudin 1 | 1.5 ± 0.06 | $2.49 \times 10^{-32}$ |
|  | Claudin 4 | 3.1 ± 0.19 | $5.93 \times 10^{-5}$ |
|  | Occludin | 3.6 ± 0.13 | $1.45 \times 10^{-14}$ |
| Epithelial Activation/Integrity | PIK3R2 | 0.43 ± 0.03 | $3.82 \times 10^{-41}$ |

TABLE 2

SAEC genes regulated by miR-126-5p with relevance to lung barrier integrity and inflammation by RNA sequencing analysis.

| Category | Gene | Fold Change | p value |
|---|---|---|---|
| Epithelial tight junction | Claudin 1 | 1.8 ± 0.03 | $1.65 \times 10^{-11}$ |
|  | Claudin 4 | 2.2 ± 0.12 | $1.56 \times 10^{-10}$ |
| Vascular permeability factor | VEGFα | 0.28 ± 0.01 | $8.34 \times 10^{-28}$ |
| Inflammatory alarmin | HMGB1 | 0.66 ± 0.02 | $2.01 \times 10^{-7}$ |

MIRNA-126-3p and 5p maintained the lung alveolar epithelial barrier integrity. The tight junction proteins claudin1, 4 and occludin expression levels affect alveolar epithelial barrier function 9Wu X, Su D., *Iran J Vet Res* 2018; 19: 35-40; Harhaj N S, Antonetti D A., *Int J Biochem Cell*

Biol 2004; 36:1206-1237). We examined the potential role of miR-126-3p and 5p in regulating epithelial barrier integrity under normal conditions and with LPS stimulation. We observed that LPS markedly decreased the mRNA expression levels of claudin1, claudin4 and occludin in SAECs (p<0.05; FIG. 13A-13E), while overexpression with either miR-126-3p or 5p attenuated these changes (p<0.05; FIG. 13A-13E). While it is not desired to be bound by any particular theory of operation, these data demonstrate that miR-126-3p and 5p may prevent the loss of epithelial tight junctions associated with ALI suggesting a possible mechanism by which EPC exosomes mitigate alveolar edema and lung injury.

Discussion of the Examples

Disclosed herein are experiments that showed that EPC exosomes imparted beneficial effects on microvascular dysfunction in CLP-induced murine sepsis. Treatment with EPC-exosomes increased survival, attenuated multi-organ failure, reduced vascular leakage, and suppressed circulating cytokine and chemokine levels. Exosomal delivery of bioactive miRNA to cells is a potential mechanism for these effects, and it was determined that miR-126-3p and 5p were highly abundant in EPC-exosomes and their expression was augmented in lung tissue by treatment with these exosomes. Moreover, it was demonstrated that EPC-exosomes could reduce VCAM1 and HMGB1 upregulation in endothelial cells through the delivery of miR-126-3p and 5p in vitro. Finally, it was discovered that EPC-exosomes no longer conferred a survival benefit in murine sepsis if they were derived from EPCs that had been previously transfected with inhibitors of miR-126-3p and 5p. Taken together, these composite data indicated that EPC-exosomes prevented microvascular dysfunction and improved sepsis outcomes potentially through the delivery of miR-126.

In recent years, considerable focus has been given to the potential role of stem or progenitor cells as a therapy for sepsis and its related organ failures[15,35]. While stem cell-based therapy is being examined in early phase clinical trials[36,37], the technical challenges involved in scaling up and maintaining stem cell colonies limit the practical use of this approach. Recent work has suggested that progenitor cells exert their beneficial effects through paracrine mechanisms including through the transmission of mediators via exosomes[16,18,38]. Stem or progenitor cell-derived exosomes possess negligible immunogenicity because, similar to their parent cells, they lack MHC class II and co-stimulatory molecules[39,40] Further, the phospholipid membranes that exosomes inherit are suited to avoid phagocytosis, degradation, and modification in circulation[41]. Thus, stem or progenitor cell-derived exosomes offer a potentially effective and pragmatic approach to novel sepsis therapy development. The data presented herein demonstrated for the first time that EPC-derived exosomes mitigated sepsis-related mortality, vascular leak, organ injury, and inflammation, possibly through the transfer of protective miR-126 strands to recipient cells, including the endothelium.

MicroRNA-126 is known to play a major role in endothelial permeability and activation. Through its targeting of Sprouty-related EVH1 Domain 1 (SPRED1) and phosphoinositol-3 kinase regulatory subunit 2 (PIK3R2), miR-126 regulates the endothelial response to vascular endothelial growth factor (VEGF) and its role in endothelial proliferation and permeability[32]. Its importance in vascular integrity has been demonstrated in both zebrafish and murine models of miR-126 deletion which demonstrate vascular leak, hemorrhage, and partial embryonic lethality[32,33]. In addition, miR-126 targets and inhibits VCAM1, a key cell adhesion molecule that modulates leukocyte binding to endothelial cells and facilitates leukocyte trafficking into inflamed tissues[42]. More recently, miR-126 was also shown to target and inhibit HMGB1[27] an inflammatory cytokine known to mediate sepsis pathophysiology and a proposed target for sepsis therapeutics[43-45]. In aggregate, miR-126 inhibits a number of targets which play critical roles in sepsis response pathways including permeability, leukocyte trafficking and cytokine-mediated inflammation.

The data presented herein suggested that EPC-derived exosomes contain abundant miR-126 which can exert paracrine effects on endothelial cells and is, at least in part, responsible for the beneficial effects of these exosomes in sepsis. This is consistent with other disease states where miR-126 has been shown to be a key paracrine mediator promoting endothelial stability[34].

In Example 9, the impact of EPC exosomes on ALI-induced alveolar epithelial damage was examined. EPC exosomes intratracheal administration attenuated lung injury through reduction of local inflammatory cytokines, pulmonary permeability, and neutrophil migration. Subsequently, we demonstrated that miR-126-3p and -5p, which are abundant in EPC exosomes, increase epithelial tight junction protein expression while decreasing target genes with relevance to ALI such as phosphoinositide-3-kinase regulatory subunit 2 (PIK3R2), HMGB1 and VEGFα.

Acute lung injury is a complex derangement of pulmonary physiology involving a number of cell types including the endothelium, epithelium and inflammatory cells such as neutrophils. Endothelial activation and dysfunction contributes to increased capillary permeability and alveolar edema and as demonstrated elsewhere herein EPC exosomes can mitigate this response through the transfer of miR-126. Here, we have demonstrated that EPC exosomes delivered intratracheally also mitigate lung injury and that these exosomes can enter epithelial cells and modulate the expression of a number of relevant genes including cytokines, VEGFα and tight junction components. These findings suggest that EPC exosomes can reduce not only endothelial but also epithelial dysfunction in ALI. Further, in the setting of improved alveolar-capillary barrier function and reduced inflammatory cytokines, neutrophil migration was also reduced in the EPC exosome-treated mice. Taken together, these data significantly enhance the potential of EPC exosomes as a therapeutic in ALI as they can impact several relevant cell types through multiple delivery approaches.

Although miR-126 expression is strongly associated with endothelial cells, it was hypothesized that it may also play a significant role in epithelial homeostasis. While it is not desired to be bound by any particular theory of operation, this hypothesis is supported by our observations that miR-126-depleted exosomes from NIH3T3 cells do not improve lung injury from LPS and that miR-126-3p and -5p increase tight junction protein expression while reducing the expression of genes related to permeability.

This Example is the first to our knowledge to identify that miR-126 delivered by EPC exosomes exerts therapeutic effects in the epithelium during ALI. While it is not desired to be bound by any particular theory of operation, EPC exosomes may exert their therapeutic potential through restoration of alveolar barrier integrity by inhibiting PIK3R2 and HMGB1 and increasing the levels of tight junction proteins including claudin1, 4 and occludin. Additionally, exosome-mediated delivery of miRNA-126-5p inhibits VEGFα expression further attenuating ALI-induced permeability. While it is not desired to be bound by any particular theory of operation, it appears that delivery of miR-126 through EPC exosomes provides a novel therapeutic in ARDS though pleiotropic effects on gene expression in a number of cell types.

This Example has limitations. Commercial kits were used to isolate exosomes and the yield may contain protein bound miRNA contamination. However, the same method was used to isolate the control NIH3T3 exosomes in order to mitigate any impact on differences between the isolated exosomes. EPC exosomes were administered 4 hours after LPS instillation in a relatively early stage of lung injury. Although we did not examine the efficacy of treating with EPC exosomes at later time points here, subject matter disclosed elsewhere herein has demonstrated that EPCs can mitigate organ injury and death when administered up to 24 hours after the onset of experimental sepsis. These data and an increasing focus on early and preventative treatment strategies for ARDS (http://petalnet.org) suggest that EPC exosomes have therapeutic potential in human ARDS. Human small airway epithelial cells may not accurately reflect the gene expression patterns of alveolar epithelial cells. SAECs are commonly used as surrogates for alveolar epithelial cells due to the challenges of isolating and maintaining the alveolar cells. We first discovered that miR-126 can upregulate the tight junction proteins and downregulate the expression levels of PIK3R2, HMGB1 and VEGFα in normal and/or LPS stimulated SAECs. The sequencing results revealed several differentially expressed genes such as SERPINB4 (serpin peptidase inhibitor), TK1 (thymidine kinase 1), CXCL14 and KLF4 (Kruppel-like factor 4) of unclear significance in ARDS but which could represent meaningful off-target effects.

This Example demonstrates that intratracheal delivery of EPC exosomes can mitigate lung injury potentially through the delivery of miR-126 to epithelial cells. This Example suggests that aerosolization could be a route of delivery.

REFERENCES

All references listed below, as well as all references cited in the instant disclosure, including but not limited to all patents, patent applications and publications thereof, scientific journal articles, and database entries (e.g., GENBANK® and miRBase database entries and all annotations available therein) are incorporated herein by reference in their entireties to the extent that they supplement, explain, provide a background for, or teach methodology, techniques, and/or compositions employed herein.

1. Freund Y, Lemachatti N, Krastinova E, Van Laer M, Claessens Y E, Avondo A, Occelli C, Feral-Pierssens A L, Truchot J, Ortega M, Carneiro B, Pernet J, Claret P G, Dami F, Bloom B, Riou B, Beaune S, French Society of Emergency Medicine Collaborators G. Prognostic Accuracy of Sepsis-3 Criteria for In-Hospital Mortality Among Patients With Suspected Infection Presenting to the Emergency Department. JAMA 2017; 317: 301-308.
2. Shankar-Hari M, Phillips G S, Levy M L, Seymour C W, Liu V X, Deutschman C S, Angus D C, Rubenfeld G D, Singer M, Sepsis Definitions Task F. Developing a New Definition and Assessing New Clinical Criteria for Septic Shock: For the Third International Consensus Definitions for Sepsis and Septic Shock (Sepsis-3). JAMA 2016; 315: 775-787.
3. Rudd K E, Delaney A, Finfer S. Counting Sepsis, an Imprecise but Improving Science. JAMA 2017; 318: 1228-1229.
4. Chen D C. Sepsis and Intestinal Microvascular Endothelial Dysfunction. Chin Med J (Engl) 2017; 130:1137-1138.
5. Alfieri A, Watson J J, Kammerer R A, Tasab M, Progias P, Reeves K, Brown N J, Brookes Z L. Angiopoietin-1 variant reduces LPS-induced microvascular dysfunction in a murine model of sepsis. Crit Care 2012; 16: R182.
6. Lu Q, Newton J, Hsiao V, Shamirian P, Blackburn M R, Pedroza M. Sustained adenosine exposure causes lung endothelial barrier dysfunction via nucleoside transporter-mediated signaling. Am J Respir Cell Mol Biol 2012; 47: 604-613.
7. Rho S S, Ando K, Fukuhara S. Dynamic Regulation of Vascular Permeability by Vascular Endothelial Cadherin-Mediated Endothelial Cell-Cell Junctions. J Nippon Med Sch 2017; 84:148-159.
8. De Backer D, Creteur J, Preiser J C, Dubois M J, Vincent J L. Microvascular blood flow is altered in patients with sepsis. Am J Respir Crit Care Med 2002; 166: 98-104.
9. Trzeciak S, Dellinger R P, Parrillo J E, Guglielmi M, Bajaj J, Abate N L, Arnold R C, Colilla S, Zanotti S, Hollenberg S M, Microcirculatory Alterations in R, Shock I. Early microcirculatory perfusion derangements in patients with severe sepsis and septic shock: relationship to hemodynamics, oxygen transport, and survival. Ann Emerg Med 2007; 49: 88-98, 98 e81-82.
10. Coletta C, Modis K, Olah G, Brunyanszki A, Herzig D S, Sherwood E R, Ungvari Z, Szabo C. Endothelial dysfunction is a potential contributor to multiple organ failure and mortality in aged mice subjected to septic shock: preclinical studies in a murine model of cecal ligation and puncture. Crit Care 2014; 18: 511.
11. Aslan A, van Meurs M, Moser J, Popa E R, Jongman R M, Zwiers P J, Molema G, Zijlstra J G. Organ-Specific Differences in Endothelial Permeability-Regulating Molecular Responses in Mouse and Human Sepsis. Shock 2017; 48: 69-77.
12. Cui B, Huang L, Fang Y, Guo R, Yin Y, Zhao X. Transplantation of endothelial progenitor cells overexpressing endothelial nitric oxide synthase enhances inhibition of neointimal hyperplasia and restores endothelium-dependent vasodilatation. Microvasc Res 2011; 81: 143-150.
13. Xu X, Yang J, Li N, Wu R, Tian H, Song H, Wang H. Role of Endothelial Progenitor Cell Transplantation in Rats With Sepsis. Transplant Proc 2015; 47: 2991-3001.
14. Guldner A, Maron-Gutierrez T, Abreu S C, Xisto D G, Senegaglia A C, Barcelos P R, Silva J D, Brofman P, de Abreu M G, Rocco P R. Expanded endothelial progenitor cells mitigate lung injury in septic mice. Stem Cell Res Ther 2015; 6: 230.
15. Fan H, Goodwin A J, Chang E, Zingarelli B, Borg K, Guan S, Halushka P V, Cook J A. Endothelial progenitor cells and a stromal cell-derived factor-1alpha analogue synergistically improve survival in sepsis. Am J Respir Crit Care Med 2014; 189: 1509-1519.
16. Li X, Chen C, Wei L, Li Q, Niu X, Xu Y, Wang Y, Zhao J. Exosomes derived from endothelial progenitor cells attenuate vascular repair and accelerate reendothelialization by enhancing endothelial function. Cytotherapy 2016; 18: 253-262.
17. Wang J, Guo R, Yang Y, Jacobs B, Chen S, Iwuchukwu I, Gaines K J, Chen Y, Simman R, Lv G, Wu K, Bihl J C. The Novel Methods for Analysis of Exosomes Released from Endothelial Cells and Endothelial Progenitor Cells. Stem Cells Int 2016: 2016: 2639728.

18. Zhang J, Chen C, Hu B, Niu X, Liu X, Zhang G, Zhang C, Li Q, Wang Y. Exosomes Derived from Human Endothelial Progenitor Cells Accelerate Cutaneous Wound Healing by Promoting Angiogenesis Through Erk1/2 Signaling. Int J Biol Sci 2016; 12: 1472-1487.
19. Valadi H, Ekstrom K, Bossios A, Sjostrand M, Lee J J, Lotvall J O. Exosome-mediated transfer of mRNAs and microRNAs is a novel mechanism of genetic exchange between cells. Nat Cell Biol 2007; 9: 654-659.
20. Ailawadi S, Wang X, Gu H, Fan G C. Pathologic function and therapeutic potential of exosomes in cardiovascular disease. Biochim Biophys Acta 2015; 1852: 1-11.
21. Ren J, He W, Zheng L, Duan H. From structures to functions: insights into exosomes as promising drug delivery vehicles. Biomater Sci 2016; 4:910-921.
22. Umezu T, Tadokoro H, Azuma K, Yoshizawa S, Ohyashiki K, Ohyashiki J H. Exosomal miR-135b shed from hypoxic multiple myeloma cells enhances angiogenesis by targeting factor-inhibiting HIF-1. Blood 2014; 124: 3748-3757.
23. Squadrito M L, Baer C, Burdet F, Madema C, Gilfillan G D, Lyle R, Ibberson M, De Palma M. Endogenous RNAs modulate microRNA sorting to exosomes and transfer to acceptor cells. Cell Rep 2014; 8: 1432-1446.
24. Chistiakov D A, Orekhov A N, Bobryshev Y V. The role of miR-126 in embryonic angiogenesis, adult vascular homeostasis, and vascular repair and its alterations in atherosclerotic disease. J Mol Cell Cardiol 2016; 97: 47-55.
25. Cerutti C, Edwards L J, de Vries H E, Sharrack B, Male D K, Romero I A. MiR-126 and miR-126* regulate shear-resistant firm leukocyte adhesion to human brain endothelium. Sci Rep 2017; 7: 45284.
26. Schober A, Nazari-Jahantigh M, Wei Y, Bidzhekov K, Gremse F, Grommes J, Megens R T, Heyll K, Noels H, Hristov M, Wang S, Kiessling F, Olson E N, Weber C. MicroRNA-126-5p promotes endothelial proliferation and limits atherosclerosis by suppressing Dlk1. Nat Med 2014; 20: 368-376.
27. Tang S T, Wang F, Shao M, Wang Y, Zhu H Q. MicroRNA-126 suppresses inflammation in endothelial cells under hyperglycemic condition by targeting HMGB1. Vascul Pharmacol 2017; 88: 48-55.
28. Helwa I, Cai J, Drewry M D, Zimmerman A, Dinkins M B, Khaled M L, Seremwe M, Dismuke W M, Bieberich E, Stamer W D, Hamrick M W, Liu Y. A Comparative Study of Serum Exosome Isolation Using Differential Ultracentrifugation and Three Commercial Reagents. PLoS One 2017; 12:e0170628.
29. Fan H, Bitto A, Zingarelli B, Luttrell L M, Borg K, Halushka P V, Cook J A. Beta-arrestin 2 negatively regulates sepsis-induced inflammation. Immunology 2010; 130: 344-351.
30. Li H, Wang S, Zhan B, He W, Chu L, Qiu D, Li N, Wan Y, Zhang H, Chen X, Fang Q, Shen J, Yang X. Therapeutic effect of Schistosoma japonicum cystatin on bacterial sepsis in mice. Parasit Vectors 2017; 10:222.
31. Beard R S, Jr., Yang X, Meegan J E, Overstreet J W, Yang C G, Elliott J A, Reynolds J J, Cha B J, Pivetti C D, Mitchell D A, Wu M H, Deschenes R J, Yuan S Y. Palmitoyl acyltransferase DHHC21 mediates endothelial dysfunction in systemic inflammatory response syndrome. Nat Commun 2016; 7:12823.
32. Fish J E, Santoro M M, Morton S U, Yu S, Yeh R F, Wythe J D, Ivey K N, Bruneau B G, Stainier D Y, Srivastava D. miR-126 regulates angiogenic signaling and vascular integrity. Dev Cell 2008; 15: 272-284.
33. Wang S, Aurora A B, Johnson B A, Qi X, McAnally J, Hill J A, Richardson J A, Bassel-Duby R, Olson E N. The endothelial-specific microRNA miR-126 governs vascular integrity and angiogenesis. Dev Cell 2008; 15: 261-271.
34. Zernecke A, Bidzhekov K, Noels H, Shagdarsuren E, Gan L, Denecke B, Hristov M, Koppel T, Jahantigh M N, Lutgens E, Wang S, Olson E N, Schober A, Weber C. Delivery of microRNA-126 by apoptotic bodies induces CXCL12-dependent vascular protection. Sci Signal 2009; 2: ra81.
35. Keane C, Jerkic M, Laffey J G. Stem Cell-based Therapies for Sepsis. Anesthesiology 2017; 127: 1017-1034.
36. Matthay M A. Therapeutic potential of mesenchymal stromal cells for acute respiratory distress syndrome. Ann Am Thorac Soc 2015; 12 Suppl 1: S54-57.
37. Wilson J G, Liu K D, Zhuo H, Caballero L, McMillan M, Fang X, Cosgrove K, Vojnik R, Calfee C S, Lee J W, Rogers A J, Levitt J, Wiener-Kronish J, Bajwa E K, Leavitt A, McKenna D, Thompson B T, Matthay M A. Mesenchymal stem (stromal) cells for treatment of ARDS: a phase 1 clinical trial. Lancet Respir Med 2015; 3: 24-32.
38. Yue Y, Garikipati V N S, Verma S K, Goukassian D A, Kishore R. Interleukin-10 Deficiency Impairs Reparative Properties of Bone Marrow-Derived Endothelial Progenitor Cell Exosomes. Tissue Eng Part A 2017; 23: 1241-1250.
39. Le Blanc K, Tammik C, Rosendahl K, Zetterberg E, Ringden O. HLA expression and immunologic properties of differentiated and undifferentiated mesenchymal stem cells. Exp Hematol 2003; 31: 890-896.
40. Cantaluppi V, Gatti S, Medica D, Figliolini F, Bruno S, Deregibus M C, Sordi A, Biancone L, Tetta C, Camussi G. Microvesicles derived from endothelial progenitor cells protect the kidney from ischemia-reperfusion injury by microRNA-dependent reprogramming of resident renal cells. Kidney Int 2012; 82: 412-427.
41. Laulagnier K, Motta C, Hamdi S, Roy S, Fauvelle F, Pageaux J F, Kobayashi T, Salles J P, Perret B, Bonnerot C, Record M. Mast cell- and dendritic cell-derived exosomes display a specific lipid composition and an unusual membrane organization. Biochem J 2004; 380: 161-171.
42. Harris T A, Yamakuchi M, Ferlito M, Mendell J T, Lowenstein C J. MicroRNA-126 regulates endothelial expression of vascular cell adhesion molecule 1. Proc Natl Acad Sci USA 2008; 105:1516-1521.
43. Wang H, Bloom O, Zhang M, Vishnubhakat J M, Ombrellino M, Che J, Frazier A, Yang H, Ivanova S, Borovikova L, Manogue K R, Faist E, Abraham E, Andersson J, Andersson U, Molina P E, Abumrad N N, Sama A, Tracey K J. HMG-1 as a late mediator of endotoxin lethality in mice. Science 1999; 285: 248-251.
44. Yang H, Ochani M, Li J, Qiang X, Tanovic M, Harris H E, Susarla S M, Ulloa L, Wang H, DiRaimo R, Czura C J, Wang H, Roth J, Warren H S, Fink M P, Fenton M J, Andersson U, Tracey K J. Reversing established sepsis with antagonists of endogenous high-mobility group box 1. Proc Natl Acad Sci USA 2004; 101: 296-301.
45. Suda K, Kitagawa Y, Ozawa S, Saikawa Y, Ueda M, Ebina M, Yamada S, Hashimoto S, Fukata S, Abraham E, Maruyama I, Kitajima M, Ishizaka A. Anti-high-mobility group box chromosomal protein 1 antibodies improve survival of rats with sepsis. World J Surg 2006; 30: 1755-1762.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. An endothelial progenitor cell-derived exosome, wherein the endothelial progenitor cell-derived exosome comprises one or more modifications that enhance expression of an miR-126 microRNA in the endothelial progenitor cell-derived exosome; and further wherein at least one of the one or more modifications comprises introduction of a heterologous nucleotide sequence that comprises, consists essentially of, or consists of, and/or that encodes, one or more of SEQ ID NOs: 1 and/or 3 into an endothelial progenitor cell from which the endothelial progenitor cell-derived exosome is derived, whereby the expression of the miR-126 microRNA in the endothelial progenitor cell-derived exosome is enhanced relative to the expression of the miR-126 microRNA in an endothelial progenitor cell-derived exosome isolated from an untreated endothelial progenitor cell-derived exosome.

2. The endothelial progenitor cell-derived exosome of claim 1, wherein the heterologous nucleotide sequence is operatively linked to one or more transcriptional regulatory sequences.

3. The endothelial progenitor cell-derived exosome of claim 1, wherein the one or more modifications comprises treating an endothelial progenitor cell from which the endothelial progenitor cell-derived exosome is derived with a stromal cell-derived factor 1 (SDF1)/C—X—C motif chemokine 12 (CXCL12) gene product and/or a mimetic thereof in an amount and for a time sufficient to enhance expression of an miR-126 microRNA in the endothelial progenitor cell-derived exosome.

4. The endothelial progenitor cell-derived exosome of claim 3, wherein the mimetic thereof is CTCE-0214 (CTCE).

5. A pharmaceutical composition comprising the endothelial progenitor cell-derived exosome of claim 1 and a pharmaceutically acceptable carrier, optionally a pharmaceutically acceptable carrier that is pharmaceutically acceptable for use in a human.

6. The pharmaceutical composition of claim 5, wherein the one or more modifications comprises treating an endothelial progenitor cell from which the endothelial progenitor cell-derived exosome is derived with a stromal cell-derived factor 1 (SDF1)/C—X—C motif chemokine 12 (CXCL12) gene product and/or a mimetic thereof in an amount and for a time sufficient to enhance expression of an miR-126 microRNA in the endothelial progenitor cell-derived exosome.

7. The pharmaceutical composition of claim 6, wherein the mimetic thereof is CTCE-0214 (CTCE).

8. The endothelial progenitor cell-derived exosome of claim 2, wherein the one or more transcriptional regulatory sequences permit expression of the heterologous nucleotide sequence in a target cell.

9. The endothelial progenitor cell-derived exosome of claim 8, wherein the target cell is an endothelial cell.

10. The endothelial progenitor cell-derived exosome of claim 9, wherein the endothelial cell is an endothelial cell that has reduced function as a consequence of sepsis.

11. The endothelial progenitor cell-derived exosome of claim 1, wherein the endothelial progenitor cell-derived exosome is derived from an endothelial cell that had been exposed to a stromal cell-derived factor 1 (SDF1)/C—X—C motif chemokine 12 (CXCL12) gene product and/or a mimetic thereof in an amount and under conditions sufficient to enhance expression of the miR-126 microRNA in the endothelial progenitor cell-derived exosome.

12. The endothelial progenitor cell-derived exosome of claim 11, wherein the mimetic thereof comprises CTCE-0214.

13. The pharmaceutical composition of claim 5, wherein the one or more modifications that enhance expression of an miR-126 microRNA in the endothelial progenitor cell-derived exosome comprises introduction of a heterologous nucleotide sequence that comprises, consists essentially of, or consists of, and/or that encodes, one or more of SEQ ID NOs: 1 and/or 3 into an endothelial progenitor cell from which the endothelial progenitor cell-derived exosome is derived.

14. The pharmaceutical composition of claim 13, wherein the heterologous nucleotide sequence is operatively linked to one or more transcriptional regulatory sequences.

15. The pharmaceutical composition of claim 14, wherein the one or more transcriptional regulatory sequences permit expression of the heterologous nucleotide sequence in a target cell.

16. The pharmaceutical composition of claim 15, wherein the target cell is an endothelial cell.

17. The pharmaceutical composition of claim 16, wherein the endothelial cell is an endothelial cell that has reduced function as a consequence of sepsis.

18. The pharmaceutical composition of claim 5, wherein the endothelial progenitor cell-derived exosome is derived from an endothelial cell that had been exposed to a stromal cell-derived factor 1 (SDF1)/C—X—C motif chemokine 12 (CXCL12) gene product and/or a mimetic thereof in an amount and under conditions sufficient to enhance expression of the miR-126 microRNA in the endothelial progenitor cell-derived exosome.

19. The pharmaceutical composition of claim 18, wherein the mimetic thereof comprises CTCE-0214.

* * * * *

SEQUENCE LISTING

<160> NUMBER OF SEQ ID NOS: 9

<210> SEQ ID NO 1
<211> LENGTH: 85
<212> TYPE: DNA
<213> ORGANISM: Homo sapiens

<400> SEQUENCE: 1
cgctggcgac gggacattat tactttggt acgcgctgtg acacttcaaa ctcgtaccgt    60
gagtaataat gcgccgtcca cggca                                         85

<210> SEQ ID NO 2
<211> LENGTH: 22
<212> TYPE: DNA
<213> ORGANISM: Homo sapiens

<400> SEQUENCE: 2
ucguaccgug aguaauaaug cg                                            22

<210> SEQ ID NO 3
<211> LENGTH: 21
<212> TYPE: DNA
<213> ORGANISM: Homo sapiens

<400> SEQUENCE: 3
cauuauuacu uuugguacgc g                                             21

<210> SEQ ID NO 4
<211> LENGTH: 14
<212> TYPE: PRT
<213> ORGANISM: Artificial sequence
<220> FEATURE:
<223> OTHER INFORMATION: synthetic peptide

<400> SEQUENCE: 4

Lys Pro Val Ser Leu Ser Tyr Arg Cys Pro Cys Arg Phe Phe
1               5                   10

<210> SEQ ID NO 5
<211> LENGTH: 13
<212> TYPE: PRT
<213> ORGANISM: Artificial sequence
<220> FEATURE:
<223> OTHER INFORMATION: synthetic peptide

<400> SEQUENCE: 5

Leu Lys Trp Ile Gln Glu Tyr Leu Glu Lys Ala Leu Asn
1               5                   10

<210> SEQ ID NO 6
<211> LENGTH: 14
<212> TYPE: PRT
<213> ORGANISM: Artificial sequence
<220> FEATURE:
<223> OTHER INFORMATION: synthetic peptide

<400> SEQUENCE: 6

Lys Pro Val Ser Leu Ser Tyr Arg Ala Pro Phe Arg Phe Phe
1               5                   10

<210> SEQ ID NO 7
<211> LENGTH: 63
<212> TYPE: DNA
<213> ORGANISM: Mus sp.

```
<400> SEQUENCE: 7
gcacauuauu acuuuuggua cgcgcuguga cacuucaaac ucguaccgug aguaauaaug    60
cgc                                                                  63

<210> SEQ ID NO 8
<211> LENGTH: 21
<212> TYPE: DNA
<213> ORGANISM: Mus sp.

<400> SEQUENCE: 8
cauuauuacu uuugguacgc g                                              21

<210> SEQ ID NO 9
<211> LENGTH: 22
<212> TYPE: DNA
<213> ORGANISM: Murs sp.

<400> SEQUENCE: 9
ucguaccgug aguaauaaug cg                                             22
```